United States Patent [19]

Schaffner et al.

[11] Patent Number: 4,508,723
[45] Date of Patent: Apr. 2, 1985

[54] 6-AZAOLIGOCYCLOALKYLME-THYLENEAMINOPENAM COMPOUNDS

[75] Inventors: Karl Schaffner, Oberwil; Riccardo Scartazzini, Basel, both of Switzerland

[73] Assignee: Ciba Geigy Corporation, Ardsley, N.Y.

[21] Appl. No.: 385,139

[22] Filed: Jun. 4, 1982

Related U.S. Application Data

[63] Continuation of Ser. No. 183,899, Sep. 4, 1980, , which is a continuation of Ser. No. 906,378, May 16, 1978, abandoned.

[30] Foreign Application Priority Data

May 17, 1977 [LU] Luxembourg .................. 77362

[51] Int. Cl.³ .................. A61K 31/38; C07D 499/32
[52] U.S. Cl. .................. 514/195; 424/271; 548/178; 514/196; 260/245.2 T
[58] Field of Search .............. 542/415, 420; 424/266, 424/271

[56] References Cited

U.S. PATENT DOCUMENTS

| | | | |
|---|---|---|---|
| 3,270,009 | 8/1966 | Flynn | 542/415 |
| 3,869,449 | 3/1975 | Godtfredsen | 424/267 |
| 3,957,764 | 5/1976 | Lund | 424/270 |
| 3,994,912 | 11/1976 | Davis et al. | 542/420 |
| 4,076,816 | 2/1978 | Tybring | 424/251 |
| 4,089,963 | 5/1978 | Bamberg et al. | 542/420 |
| 4,278,792 | 7/1981 | Cesti et al. | 542/420 |
| 4,325,960 | 4/1982 | Godtfredsen et al. | 542/420 |
| 4,341,779 | 7/1982 | Cieslak et al. | 542/420 |
| 4,345,071 | 8/1982 | Binderup | 542/420 |

FOREIGN PATENT DOCUMENTS

| | | |
|---|---|---|
| 2430375 | 3/1975 | Fed. Rep. of Germany . |
| 1312030 | 4/1973 | United Kingdom . |
| 1315566 | 5/1973 | United Kingdom . |
| 1405886 | 9/1975 | United Kingdom . |
| 1417099 | 12/1975 | United Kingdom . |
| 1427139 | 3/1976 | United Kingdom . |
| 1482388 | 8/1977 | United Kingdom . |

Primary Examiner—Glennon H. Hollrah
Assistant Examiner—James H. Turnipseed
Attorney, Agent, or Firm—Irving N. Feit

[57] ABSTRACT

6-Amino-penam compounds, having an antimicrobial action, of the formula

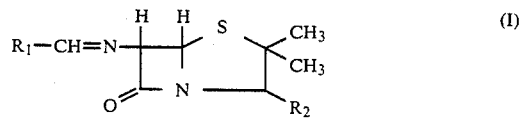

in which $R_1$ is an azaoligocycloalkyl radical which is bonded via the ring nitrogen atom and contains at least one endo-bridge atom and a total of 7 to 12 ring atoms and can contain a double bond and/or, if desired, as a further ring hetero-atom, an oxygen atom, or a nitrogen atom which can link the radical $X_1$, where $X_1$ is hydrogen or lower alkyl, and/or, if desired, free, esterified or etherified hydroxyl which is bonded to a ring carbon atom, and in which $R_2$ is free carboxyl or carboxyl esterified by a physiologically detachable group, and salts of such compounds, processes for their preparation, pharmaceutical preparations which contain these compounds, including mixtures of these compounds with other antimicrobial, especially antibacterial and/or antiviral, active ingredients and/or additional substances or substance mixtures which alleviate the symptoms in the case of infections, the use of the novel compounds of the formula I and their salts, and of the novel substance mixtures, for combating micro-organisms and the preparation of corresponding medicaments by non-chemical means.

18 Claims, No Drawings

6-AZAOLIGOCYCLOALKYLMETHYLENEAMINOPENAM COMPOUNDS

This is a continuation of application Ser. No. 183,899 filed on Sept. 4, 1980 which in turn is a continuation of application Ser. No. 906,378 filed May 16, 1978, now abandoned.

The invention relates to novel therapeutically valuable 6-amino-penam compounds, processes for their preparation and pharmaceutical preparations which contain the novel compounds, and also the use thereof.

The novel 6-amino-penam compounds are those of the formula

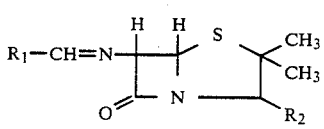

(I)

in which $R_1$ is an azaoligocycloalkyl radical which is bonded via the ring nitrogen atom and contains at least one endo-bridge atom and a total of 7 to 12 ring atoms and can contain a double bond and/or, if desired, as a further ring hetero-atom, an oxygen atom, or a nitrogen atom which can link the radical $X_1$, where $X_1$ is hydrogen or lower alkyl, and/or, if desired, free, esterified or etherified hydroxyl which is bonded to a ring carbon atom, and in which $R_2$ is free carboxyl or carboxyl esterified by a physiologically detachable group, and salts of such compounds.

The radical $R_1$ is in particular corresponding aza-bi- and aza-tri-cycloalkyl having a total of 8 to 11 ring atoms.

Radicals of this type are, in particular, corresponding azabicycloalkyl or azabicycloalkenyl, such as corresponding azabicyclooctyl, for example 8-azabicyclo[3.2.1]-oct-8-yl (for example in particular a nortropane radical bonded in the 8-position) and 2-azabicyclo[2.2.2]oct-2-yl, or corresponding azabicyclononyl, especially 3-azabicyclo[3.2.2]non-3-yl and 9-azabicyclo[3.3.1]non-9-yl (for example a granatanine radical bonded in the 9-position); corresponding oxaazabicycloalkyl or diazabicycloalkyl, such as corresponding oxaaza- or diazabicyclononyl, especially 3,7-diazabicyclo[3.3.1]non-3-yl (for example a bispidine radical bonded in the 3-position); corresponding azatricycloalkyl, such as azatricyclodecyl, especially 2-azatricyclo[3.3.1.1.$^{3,7}$]dec-2-yl, 4-azatricyclo[5.2.1.0$^{2,6}$]dec-4-yl or 3-azatricyclo[5.2.1.0$^{1,5}$]dec-3-yl, or azatricycloundecyl, especially 4-azatricyclo[5.2.2.0$^{2,6}$]undec-4-yl or 8-azatricyclo[4.3.2.0$^{1,6}$]undec-8-yl; corresponding azatricycloalkenyl, such as azatricyclodecenyl, especially 4-azatricyclo[5.2.1.0$^{2,6}$]dec-8-en-4-yl, and also azatricycloundecenyl, especially 4-azatricyclo[5.2.2.0$^{2,6}$]undec-8-en-4-yl or 8-azatricyclo[4.3.2.0$^{1,6}$]undec-3-en-8-yl; corresponding oxaazatricycloalkyl, such as oxaazatricyclodecyl, especially 10-oxa-3-azatricyclo[5.2.1.0$^{1,5}$]dec-3-yl or 10-oxa-4-azatricyclo[5.2.1.0$^{2,6}$]dec-4-yl, and corresponding diazatricycloalkyl, for example 3,10-diazatricyclo[5.2.1.0$^{1,5}$]dec-3-yl.

The above compounds have been named in accordance with the currently valid nomenclature which has been laid down by the IUPAC (International Union of Pure and Applied Chemistry) and a commentary on which is given, for example, in D. Hellwinkel ("Die systematische Nomenklatur der organischen Chemie" ("Systematic Nomenclature in Organic Chemistry"), Springer-Verlag, Berlin, 1974, pages 23–28).

Particularly preferred radicals $R_1$ are the radicals which are bonded via the ring nitrogen and are derived from substituted or unsubstituted nortropane, granatanine, bispidine, 2-azabicyclo[2.2.2]octane and 3-azabicyclo[3.2.2]nonane, and also, in particular, the radicals derived from an azatricycloalkane, such as 7-azatricyclo[5.2.2.0$^{2,6}$]undecane and from an azatricycloalkene, such as 7-azatricyclo[5.2.2.0$^{2,6}$]undec-8-ene.

An additional ring nitrogen atom which may be present is either bonded by all three valencies in the ring system, in which case it can be present as a bridge head atom or can participate in a ring double bond, or is bonded, by its third valency, to a radical $X_1$ which is outside the ring and is hydrogen or lower alkyl.

In this specification, radicals qualified by the term "lower" contain 1 to 8 and preferably 1 to 4 carbon atoms.

Lower alkyl is, for example, in particular methyl, ethyl, n-propyl, isopropyl, n-butyl, isobutyl, sec.-butyl or tert.-butyl, and also n-pentyl, n-hexyl, n-heptyl or n-octyl.

The radical $X_1$ is preferably methyl.

The azaoligocycloalkyl radical $R_1$ can be substituted by a free, esterified or etherified hydroxyl which is bonded to any desired ring carbon atom, preferred ring carbon atoms being those which are not a bridge head atom and especially those which are separated by 1–3 ring atoms from the aza nitrogen atom which bonds the radical $R_1$ to the penicilliminomethylene radical; for example, the free, esterified or etherified hydroxyl is preferably in the 3-position in 8-azabicyclo[3.2.1]oct-8-yl, preferably in the 9-position in 3,7-diazabicyclo[3.3.1]non-3-yl and preferably in the 3- or 7-position in 9-azabicyclo[3.3.1]non-9-yl.

An esterified hydroxyl is acyloxy or hydroxyl esterified by a hydrogen halide acid, i.e. halogen.

Halogen is in particular chlorine or bromine and also iodine or fluorine.

Acyl is the monovalent acyl radical of a carboxylic acid, of a carbonic acid half-derivative or of a sulphonic acid, preferably having up to 18 carbon atoms, especially the monovalent acyl radical of a substituted or unsubstituted aliphatic carboxylic acid or of a substituted or unsubstituted aromatic-aliphatic, aromatic, heterocyclic-aliphatic or heterocyclic carboxylic acid and also the monovalent acyl radical of a carbonic acid half-derivative or of a substituted aliphatic or aromatic sulphonic acid.

Substituted or unsubstituted aliphatic carboxylic acids are, in particular, lower alkanecarboxylic acids which are unsubstituted or substituted by carboxyl, lower alkoxycarbonyl, carbamoyl or carbamoyl substituted by lower alkyl, and/or by substituted or unsubstituted basic amino. Substituted or unsubstituted basic amino is, in particular, amino, mono- or di-lower alkylamino or amino cyclically disubstituted by lower alkylene or by lower alkylene interrupted by one of the groups O, NH or N-lower alkyl. Lower alkylene contains up to 6, and preferably 4–5, carbon atoms and is, for example, tetramethylene, pentamethylene or hexamethylene, whilst lower alkylene interrupted by a hetero-group is in particular oxa-lower alkylene, for example 3-oxa-pentamethylene, and aza-lower alkylene, for example 3-azapentamethylene or 3-methyl-3-azapentamethylene.

Substituted or unsubstituted aromatic-aliphatic carboxylic acids are in particular phenyl-lower alkanecarboxylic acids which are unsubstituted or substituted by lower alkyl, halogen, lower alkoxy or especially carboxyl, lower alkoxycarbonyl or carbamoyl in the phenyl radical or are unsubstituted or substituted by amino or hydroxyl in the lower alkane side chain. Substituted or unsubstituted aromatic carboxylic acids are, in particular, benzoic acids which are unsubstituted or substituted, like the above aromatic-aliphatic carboxylic acids, in the phenyl radical. Substituted or unsubstituted heterocyclic-aliphatic carboxylic acids are, in particular, corresponding α-amino acids.

Substituted or unsubstituted heterocyclic carboxylic acids are derived, in particular, from mono-, di- or tri-azacyclic six-membered ring compounds which are unsubstituted or monosubstituted or disubstituted by hydroxyl, such as pyridine, pyrimidine, pyrazine, pyridazine or triazine, and also from thiophene or furane.

The monovalent acyl radical of a carbonic acid half-derivative is, for example, lower alkoxycarbonyl which is unsubstituted or substituted, such as monosubstituted to trisubstituted by halogen, especially chlorine, and also carbamoyl which is unsubstituted or monosubstituted or disubstituted by lower alkyl.

Substituted or unsubstituted aliphatic sulphonic acids are, in particular, corresponding lower alkanesulphonic acids, and also lower alkanesulphonic acids which are unsubstituted or substituted by amino or substituted basic amino, as defined above, and are derived therefrom, such as methanesulphonic acid or taurine. Aromatic sulphonic acids are substituted or unsubstituted benzene- or naphthalene-sulphonic acids, for example benzenesulphonic acid, toluenesulphonic acid, such as o- or p-toluenesulphonic acid, or naphthalenesulphonic acid, such as α- or β-naphthalenesulphonic acid.

Examples of esterified hydroxyl groups are halogen, for example chlorine or bromine, lower alkanoyloxy, for example formyloxy, acetoxy or pivaloyloxy, and also substituted lower alkanoyloxy, such as lower alkanoyloxy substituted by carboxyl, lower alkoxycarbonyl, for example methoxycarbonyl, or amino, which can be disubstituted by lower alkyl, for example dimethylamino, for example carboxyacetoxy, methoxycarbonylacetoxy or dimethylamino-acetoxy, and also substituted lower alkanoyloxy radicals derived from naturally occurring amino acids and their D- and D,L-stereoisomers, for example glycyloxy, alanyloxy or β-alanyloxy, and also phenyl-lower alkanoyloxy, which is unsubstituted or substituted by amino or hydroxyl, for example phenylacetoxy, phenylglycyloxy or mandeloyloxy, benzoyloxy which is unsubstituted or substituted by carboxyl, for example benzoyloxy or o- or p-carboxybenzoyloxy, pyridine-, pyrimidine- or pyridazine-carbonyloxy which is unsubstituted or monosubstituted to disubstituted by hydroxyl, for example pyridylcarbonyloxy, such as nicotinoyloxy, 2,6-dihydroxy-4-pyrimidylcarbonyloxy, 2,4-dihydroxy-5-pyrimidylcarbonyloxy or 3-hydroxy-6-pyridazinylcarbonyloxy, it being possible for the last-mentioned hydroxysubstituted radicals also to be in their tautomeric hydroxyoxo or oxo forms, and lower alkoxycarbonyloxy which is unsubstituted or monosubstituted to trisubstituted by chlorine, for example methoxycarbonyloxy or trichloroethoxycarbonyloxy, carbamoyloxy which is unsubstituted or monosubstituted or disubstituted by lower alkyl, for example carbamoyloxy or N,N-dimethylcarbamoyloxy, substituted or unsubstituted lower alkanesulphonyloxy, for example methanesulphonyloxy, and aromatic sulphonyloxy, for example benzenesulphonyloxy, o- or p-toluenesulphonyloxy or α- or β-naphthalenesulphonyloxy.

An etherified hydroxyl group is substituted or unsubstituted lower alkoxy, such as substituted or unsubstituted methoxy or ethoxy, or phenoxy. Substituted lower alkoxy is, for example, substituted by lower alkoxy, by halogen, by carboxyl, by the substituted or unsubstituted basic amino radicals defined above or by up to three phenyl or anisyl radicals.

Examples of etherified hydroxyl groups are methoxy, ethoxy, benzyloxy, benzhydryloxy, trityloxy and also carboxylower alkoxy, such as 2-carboxymethoxy or 2-carboxypropoxy, or lower alkoxy substituted by one of the basic amino groups defined above, such as 2-aminoethoxy, 2-aminoisopropoxy, dimethylaminoethoxy, 2-piperidinoethoxy, 2-morpholinoisopropoxy or 2-(4-methylpiperazino)-ethoxy.

The radical $R_2$ can be carboxyl or a carboxyl esterified by a physiologically detachable group.

A carboxyl group esterified by a physiologically detachable group can be any desired physiologically detachable and physiologically acceptable esterified carboxyl group which is known per se and is, for example, lower alkoxycarbonyl substituted by amino, di-lower alkylamino or acylamino, for example β-aminoethoxycarbonyl, β-dimethylaminoethoxycarbonyl, β-acetamidoethoxycarbonyl or β-carbamoylethoxycarbonyl, but preferably a group of the general formula

in which $R_3$ is hydrogen or a lower alkyl radical having 1–3 carbon atoms, especially hydrogen and methyl, $R_4$ is the acyl radical of a substituted or unsubstituted carboxylic acid, such as of a corresponding mono-, di- or poly-carboxylic acid, of a carbonic acid half-derivative or of an aliphatic or aromatic sulphonic acid having up to 18 carbon atoms, and also lower alkyl substituted by hydroxyl, lower alkoxy, for example methoxy, amino or di-lower alkylamino, such as dimethylamino, cycloalkyl having 3–7 carbon atoms, phenyl which is unsubstituted or substituted by chlorine, hydroxyl or methoxy, or correspondingly substituted phenyl-lower alkyl, such as corresponding benzyl or α-phenylethyl, or a five-membered or six-membered heterocyclic structure which can be hydrogenated and can be benzo-condensed and has 1–2 ring oxygen, sulphur or nitrogen atoms in the position adjacent to the bonding carbon atom, and Z is an ether, thioether, sulphinyl, sulphonyl, imino, lower alkylimino or acylimino group or a group of the formula

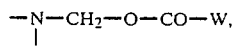

in which —O—CO—W is the radical of a carboxyl compound which has an antibiotic or antibacterial action and is bonded via the carboxyl group, especially the radical of a corresponding antibiotic from the penam or cephem series, for example the corresponding radical of a compound of the formula I, or the radical of an amoxycillin or ampicillin, or in which the grouping —CH(R$_3$)—Z—R$_4$ or —Z—R$_4$ is a constituent of a heterocyclic ring system.

Examples of such esterified carboxyl groups of the formula (A) which are particularly easily splittable under physiological conditions and are physiologically acceptable are known from numerous patent specifications.

Preferred groups (A) are, for example, those in which R$_3$ is hydrogen or methyl, Z is oxygen or sulphur and R$_4$ is the substituted or unsubstituted acyl radical of a monocarboxylic acid, for example lower alkanoyl which is unsubstituted or substituted by hydroxyl, lower alkoxy, such as methoxy, halogen, such as chlorine, lower alkylthio, such as methylthio, amino or di-lower alkylamino, such as dimethylamino, for example acetyl, pivaloyl, glycyl, L-valyl, L-leucyl, L-seryl, methoxyacetyl or methylthioacetyl, cyclopropylcarbonyl, benzoyl, chlorobenzoyl, p-(N,N-diisopropylaminosulphonyl)-benzoyl, thienylcarbonyl, furylcarbonyl, acryloyl, the radical of a carbonic acid half-derivative, such as of a carbonic acid half-ester or half-amide, for example carbamoyl, N,N-dimethylcarbamoyl, lower alkoxycarbonyl, for example methoxycarbonyl or ethoxycarbonyl, or lower alkylthiocarbonyl, such as ethylthiocarbonyl, or the acyl radical —CO—W of a carboxyl compound having an antibiotic or antibacterial action, for example of a corresponding penam or cephem compound, such as one of those mentioned in German Offenlegungsschrift No. 2,713,683, Belgian Pat. Nos. 781,659 and 853,607 and in French Patent Specification No. 2,290,443, or in which R$_4$ is lower alkyl which is unsubstituted or substituted as above, such as corresponding methyl or ethyl, for example methoxymethyl, ethoxymethyl, β-hydroxyethyl, β-aminoethyl or β-dimethylaminoethyl.

A further preferred group of esterified carboxyl groups (A) which are easily splittable under physiological conditions are those in which R$_3$ is hydrogen or methyl, Z is imino, lower alkylimino or the group

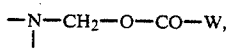

which is as defined above, and R$_4$ is the radical of a carbonic acid half-ester or half-thioester, for example one of these mentioned above, or a lower alkanoyl radical which is unsubstituted or substituted as above, for example corresponding acetyl. Such groups are known, for example, from British Pat. Nos. 1,454,726 and 1,458,234.

A further preferred group (A) is that in which the grouping —CH(R$_3$)—Z—R$_4$ is a constituent of a heterocyclic ring system which, together with the oxycarbonyl group, forms a group (A), for example 5-oxo-dihydro-2-furfuryloxycarbonyl, 5-oxo-tetrahydro-2-furfuryloxycarbonyl, phthalidyloxycarbonyl or 5,6-dimethoxyphthalidyloxycarbonyl.

The grouping —Z—R$_4$ can also be a constituent of a heterocyclic ring system and is then, for example, a diacylimino group, such as a succinylimino, saccharimido or phthalimido group, which together with the radical —CO—O—CH(R$_3$)— forms a group (A), for example the succinyliminomethoxycarbonyl, saccharimidomethoxycarbonyl or phthalimidomethoxycarbonyl group.

A further preferred group (A) is that in which R$_3$ is hydrogen or methyl, Z is sulphinyl or sulphonyl and R$_4$ is as defined above and in particular is lower alkyl which is unsubstituted or substituted as above, especially corresponding methyl or ethyl. Such radicals (A) are described, for example, in Belgian Pat. Nos. 788,720, 827,858 and 831,941.

In addition to the basic amidino group R$_1$—CH=N— and a free carboxyl group R$_2$, compounds of the formula I can contain further salt-forming radicals, i.e. basic and/or acid radicals, in the esterified or etherified hydroxyl group which can be a substituent of the group R$_1$, and, according to the particular predominant neutral, basic or acid character in the total molecule, can form inner, zwitterionic salts and/or external salts with acids or bases.

In the absence of external salt-forming anions or cations, compounds of the formula I which contain acid and basic groups are in the form of inner salts, i.e. in the form of zwitterions. Compounds of the formula I which have a predominantly basic character, for example those in which R$_2$ is carboxyl esterified by a physiologically detachable group, can form stable acid addition salts, for example with inorganic acids, such as hydrochloric acid, sulphuric acid or phosphoric acid, or with suitable organic carboxylic or sulphonic acids, such as with aliphatic mono-, di- or tri-carboxylic acids, for example acetic acid, malonic acid, tartaric acid, embonic acid, citric acid or 4-(N,N-dipropylsulphamoyl)-benzoic acid (Probenecid), or with p-toluenesulphonic acid, α- or β-naphthalenesulphonic acid or naphthalene-disulphonic acid, especially naphthalene-1,5-disulphonic acid, or with cation exchangers. Compounds of the formula I which have a predominantly acid character can form stable salts with bases. Preferred salts of this type are, in particular, pharmaceutically acceptable non-toxic salts, such as alkali metal salts or alkaline earth metal salts, for example sodium salts, potassium salts, magnesium salts or calcium salts, and also ammonium salts with ammonia or suitable organic amines, the compounds used for forming the salts being, in particular, aliphatic, cycloaliphatic, cycloaliphatic-aliphatic and araliphatic primary, secondary or tertiary mono-, di- or poly-amines, and also heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)amine, basic aliphatic esters of carboxylic acids, for example 2-diethylaminoethyl 4-aminobenzoate, lower alkyleneamines, for example 1-ethyl-piperidine, cycloalkylamines, for example dicyclohexylamine, or benzylamines, for example N,N'-dibenzylethylenediamine, and also bases of the pyridine type, for example pyridine, collidine or quinoline, as well as salts with anion exchangers.

The novel compounds can be in the form of mixtures of isomers, for example in the form of racemates, or in the form of pure isomers, for example in the form of optically active antipodes or in the form of the syn- or anti-compound.

The novel compounds of the formula I and their salts have a valuable pharmacological action, especially a particularly pronounced antimicrobial, especially antibacterial, action. For example, they are active against micro-organisms, such as against Gram-positive bacteria, for example *Staphylococcus aureus*, in minimum inhibitory concentrations (MIC) in vitro of from about 0.0125 mg/ml, but in particular against Gram-negative bacteria, especially entero-bacteria, such as those mentioned below, in the dosage range of about 0.0002 to about 0.05 mg/ml.

For example in doses above about the MIC values indicated below, they are active in vitro against the following Gram-negative micro-organisms: *Klebsiella pneumoniae* (0.0008 mg/ml), *Salmonella typhimurium* (0.0004 mg/ml), *Neisseria* species, for example *Neisseria gonorrhoeae* (0.0002 mg/ml) and *Neisseria meningitidis* (0.0004 mg/ml), and *Aerobacter* species, for example *Aerobacter cloacae* (0.0008 mg/ml), and especially against pathogenic strains of *Escherichia coli* (0.0004 mg/ml). They are also active in vivo, for example in mice infected with *E. coli*, when administered in the dosage range of about 10 to about 70 mg/kg (subcutaneously) or of about 20 to about 150 mg/kg (perorally).

A further outstanding property of the novel compounds is the excellent action against influenza viruses, especially those of type A, for example against the strains Victoria 3/75 and Hongkong 1/68, which can be demonstrated in mice, in vivo, in a concentration range of from 1 mg/kg and especially in the range of 10 mg/kg to 250 mg/kg (perorally) or on 30 minute inhalation of a 1% strength aerosol, corresponding to 0.5 mg/mouse (per inhalation).

The compounds according to the invention are also distinguished by the fact that, in mixtures with known antimicrobial, such as antibacterial, antimycotic or antiviral, substances, for example with known antibiotics, especially β-lactam antibiotics, such as those of the penam or cephem series, and also with aminoglycoside or other antibacterial active ingredients, for example those mentioned below, they display, in a dosage range of about 0.1–500 mg/kg, administered perorally, or 0.1–500 mg/kg administered parenterally, for example i.v., i.m., i.p. or s.c., of a compound of the formula I and in a mixing ratio of 1:29 to 29:1, preferably in a mixing ratio of 1:5 to 5:1, an activity which complements the antimicrobial spectrum of action or in some cases is synergistic.

For example, the compounds of the formula I, especially 6β-[(4-endo-azatricyclo[5.2.2.0$^{2,6}$]undec-8-enyl)-methyleneamino]-penicillanic acid and pivaloyloxymethyl 6β-[(4-azatricyclo[5.2.2.0$^{2,6}$]undec-8-enyl)-methyleneamino]-penicillanate, can be administered as a mixture with, and conjointly with, a β-lactam antibiotic, such as one of the penicillins amoxycillin, ampicillin, azlocillin, bacampicillin, mezlocillin, penicillin G, penicillin V, piperacillin or pivampicillin, one of the cephalosporin antibiotics cephacetrile, cephalexin, cefamandole, Cefasulbamid, cefazolin, cefoxitin, cefuroxime, 7β-(1,4-cyclohexadienylglycylamido)-3-methoxy-3-cephem-4-carboxylic acid or 7β-[4-(2-iminothiazolidinyl)-acetamido]-3-[1-(2-dimethylaminoethyl)-tetrazolylthiomethyl]-3-cephem-4-carboxylic acid, or 7β-[3-(methylsulphonylaminophenyl)-glycylamido]-3-methoxy-3-cephem-4-carboxylic acid or an aminoglycoside antibiotic, such as amikacin, gentamicin, sisomicin, Netilmicin or tobramycin, a macrolide antibiotic such as erythromycin, a sulphonamide, such as sulfamethoxazole, sulfametrole or sulfamethizole, or a mixture of a sulphonamide and trimethoprim, for example a mixture of sulfamethoxazole and trimethoprim (5:1) or of sulfametrole and trimethoprim (5:1), and also with another synthetic antibacterial agent, such as trimethoprim or an antiviral agent, such as those of the adamantane type, for example 1-aminoadamantane hydrochloride.

Especially for the treatment of colds, and in particular of influenza and the bacterial infections preceding, accompanying or following this, the compounds, according to the invention, of the formula I, especially 6β-[(4-endo-azatricyclo[5.2.2.0$^{2,6}$]undec-8-enyl)-methyleneamino]-penicillanic acid or its physiologically acceptable salts or its physiologically easily splittable esters, such as the pivaloyloxymethyl ester, can be used as a mixture with one or more antimicrobial active ingredients which are customary and effective in the case of such infections, such as those substances mentioned above and/or additional symptom-alleviating substances or mixtures of active ingredients, in particular in a mixing ratio of 1:10 to 10:1. Antimicrobial active ingredients particularly suitable for this purpose are, for example, other compounds having an antiviral action, such as those of the adamantane type, for example 1-aminoadamantane, 1-(1-aminoethyl)-adamantane, 1'-methyl-spiro[adamantane-2,3'-pyrrolidine], 1-(ethoxymethylcarbonylamino)-adamantane or 1-(2-dimethylaminoethoxy-methylcarbonylamino)-adamantane or non-toxic salts, for example hydrochlorides, thereof, and also antibacterial active ingredients which are active against infections of the respiratory passages, such as ampicillin, bacampicillin, dihydroampicillin, amoxicillin, penicillin G, penicillin V, cefamandole, 7β-[4-(2-iminothiazolidinyl)acetamido]-3-[1-(2-dimethylaminoethyl)-tetrazol-5-yl-thiomethyl]-3-cephem-4-carboxylic acid, erythromycin, Netilmycin, tobramycin, sulfamethoxazole, trimethoprim or a mixture of sulfamethoxazole and trimethoprim (5:1) or their physiologically acceptable salts. Suitable symptom-alleviating substances are, in particular, compounds which have proved useful in infections of the respiratory passages and which facilitate breathing, or mixtures thereof.

The compound of the formula I having an antiviral action can be combined in a mixture with further antimicrobial active ingredients, a symptom-alleviating compound and/or suitable pharmaceutical carriers to give combination preparations, which can be administered in the manner customary in the case of infectious diseases of the respiratory passages, for example also in the form of nosedrops, an inhalation spray, a syrup or lozenges.

The symptom-alleviating substances are known substances which facilitate breathing, in particular menthol, such as l-menthol, and are used in particular for spray (inhalation) administration.

The present invention relates preferably to those compounds of the formula I in which $R_1$ is aza-bi- or -tri-cycloalkyl which is unsubstituted or substituted by hydroxyl or esterified or etherified hydroxyl, and also can contain, as a further ring hetero-atom, oxygen, or nitrogen which can bond the radical $X_1$, and/or a double bond, from the preferred group of aza-bi- and -tri-cycloalkyls having 8 to 11 ring atoms, which is mentioned below, and $R_2$ is free carboxyl or carboxyl esterified by a physiologically detachable group, especially carboxyl or a carboxyl group, esterified by a physiologically detachable group, of the formula (A) in particular having the given meanings, which are likewise preferred, or salts, especially pharmaceutically acceptable salts, of such compounds having salt-forming groups. In the abovementioned preferred group of compounds of the formula I, the azaoligocyclyl radical $R_1$ is a corresponding bi- or tri-cyclic ring system having 8–11 ring members, especially corresponding azabicycloalkyl or azabicycloalkenyl, such as corresponding azabicyclooctyl, for example 8-azabicyclo[3.2.1]oct-8-yl (for example in particular a nortropane radical bonded in the 8-position) and 2-azabicyclo[2.2.2]oct-2-yl, or corresponding azabicyclononyl, especially 3-azabicyclo[3.2.2]non-3-yl and 9-azabicyclo[3.3.1]non-9-yl (for example a granatanine radical bonded in the 9-position); corresponding oxaazabicycloalkyl or diazabicycloalkyl, such as corresponding oxaaza- or diaza-bicyclononyl, especially 3,7-diazabicyclo[3.3.1]non-3-yl (for example a bis-pidine radical bonded in the 3-position); corresponding azatricycloalkyl, such as azatricyclodecyl, especially 2-azatricyclo[3.3.1.1$^{3,7}$]dec-2-yl, 4-azatricyclo[5.2.1.0$^{2,6}$]dec-4-yl or 3-azatricyclo[5.2.1.0$^{1,5}$]dec-3-yl, or azatricycloundecyl, especially 4-azatricyclo[5.2.2.0$^{2,6}$]undec-4-yl or 8-azatricyclo [4.3.2.0$^{1,6}$]undec-8-yl; corresponding azatricycloalkenyl, such as azatricyclodecenyl, especially 4-azatricyclo[5.2.1.0$^{2,6}$]dec-8-en-4-yl, and also azatricycloundecenyl, especially 4-azatricyclo[5.2.2.0$^{2,6}$]undec-8-en-4-yl or 8-azatricyclo[4.3.2.0$^{1,6}$]undec-3-en-8-yl; corresponding oxaazatricycloalkyl, such as oxaazatricyclodecyl, especially 10-oxa-3-azatricyclo[5.2.1.0$^{1,5}$]dec-3-yl or 10-oxa-4-azatricyclo[5.2.1.0$^{2,6}$]dec-4-yl, and corresponding diazatricycloalkyl, for example 3,10-diazatricyclo[5.2.1.0$^{1,5}$]dec-3-yl.

The invention relates especially to those compounds of the formula I in which $R_1$ is an azabicycloalkyl having 8–11 ring members which is bonded via the ring nitrogen atom and substituted by hydroxyl, esterified hydroxyl, such as hydroxyl esterified by a hydrogen halide, for example chlorine or bromine, lower alkanoyloxy, which is unsubstituted or substituted by carboxyl, lower alkoxycarbonyl or carbamoyl or by substituted or unsubstituted basic amino, or benzoyloxy, which is unsubstituted or substituted by carboxyl, pyridine-, pyrimidine- or pyridazine-carbonyloxy, which is unsubstituted or substituted by one or two hydroxyl radicals, lower alkoxycarbonyloxy, which is unsubstituted or monosubstituted to trisubstituted by chlorine, carbamoyloxy, which is unsubstituted or monosubstituted or disubstituted by lower alkyl, lower alkanesulphonyloxy, or aromatic sulphonyloxy, or etherified hydroxyl, such as lower alkoxy substituted by lower alkoxy, phenoxy, halogen, especially chlorine or bromine, carboxyl or the basic amino radicals defined above and also by up to three phenyl or anisyl radicals, such as a corresponding azabicyclooctyl, especially 8-aza-bicyclo[3.2.1]oct-8-yl, and $R_2$ is carboxyl or an esterified carboxyl group, which is easily splittable under physiological conditions and has been mentioned above as being preferred, of the formula (A), in which $R_3$ is hydrogen or methyl, Z is oxygen and $R_4$ is lower alkyl which is unsubstituted or substituted by amino or di-lower alkylamino, for example methyl, ethyl, $\beta$-aminoethyl or $\beta$-dimethylaminoethyl, lower alkanoyl which is unsubstituted or substituted by amino or di-lower alkylamino, for example acetyl, pivaloyl, glycyl, L-valeryl or L-leucyl, lower alkoxycarbonyl, for example methoxycarbonyl or ethoxycarbonyl, or carbamoyl, or in which the radical (A) is phthalidyloxycarbonyl, and also salts, especially pharmacologically acceptable salts, of such compounds.

The invention also relates in particular to compounds of the formula I in which $R_1$ is an azabicycloalkyl which is bonded via the aza ring nitrogen atom and contains 8–11 ring members, such as corresponding azabicyclooctyl, for example 8-azabicyclo[3.2.1]oct-8-yl (for example in particular a nortropane radical bonded in the 8-position) and 2-azabicyclo[2.2.2]oct-2-yl, or corresponding azabicyclononyl, especially 2-azabicyclo[3.2.2]non-3-yl and 9-azabicyclo[3.3.1]non-9-yl (for example a granatanine radical bonded in the 9-position); corresponding oxaazabicycloalkyl or diazabicycloalkyl, such as corresponding oxaaza- or diaza-bicyclononyl, especially 3,7-diazabicyclo[3.3.1]non-3-yl (for example a bispidine radial bonded in the 3-position); corresponding azatricycloalkyl, such as azatricyclodecyl, especially 2-azatricyclo[3.3.1.1$^{3,7}$]dec-2-yl, or azatricycloundecyl, especially 4-azatricyclo[5.2.2.0$^{2,6}$]undec-4-yl; corresponding azatricycloalkenyl, such as azatricycloundecenyl, especially 4-endo-azatricyclo[5.2.2.0$^{2,6}$]undec-8-en-4-yl; corresponding oxaazatricycloalkyl, such as oxaazatricyclodecyl, especially 10-oxa-3-azatricyclo[5.2.1.0$^{1,5}$]dec-3-yl and corresponding diazatricycloalkyl, for example 3,10-diazatricyclo[5.2.1.0$^{1,5}$]dec-3-yl, the second nitrogen atom in the abovementioned diaza compounds preferably carrying a radical $X_1$, especially methyl, and $R_2$ is carboxyl, substituted or unsubstituted lower alkanoyloxymethoxycarbonyl, such as acetyloxymethoxycarbonyl, pivaloyloxymethoxycarbonyl, $\alpha$-pivaloyloxyethoxycarbonyl, glycyloxymethoxycarbonyl, L-valyloxymethoxycarbonyl or L-leucyloxymethoxycarbonyl, substituted or unsubstituted lower alkoxymethoxycarbonyl, such as methoxymethoxycarbonyl, ethoxymethoxycarbonyl, $\alpha$-methoxyethoxycarbonyl, methoxycarbonyloxymethoxycarbonyl, $\alpha$-(ethoxycarbonyloxy-ethoxycarbonyl, carbamoyloxymethoxycarbonyl or phthalidyloxymethoxycarbonyl, and also salts, especially pharmacologically acceptable salts, of such compounds.

The invention relates especially to compounds of the formula I in which $R_1$ is an 8-azabicyclo[3.2.1]oct-8-yl, 3-azabicyclo[3.2.2]non-3-yl, 9-azabicyclo[3.3.1]non-9-yl, 7-methyl-3,7-diazabicyclo[3.3.1]non-3-yl, and in the first line azatricycloalkyl and azatricycloalkenyl, such as 2-azatricyclo[3.3.1.1$^{3,7}$]dec-2-yl, 4-azatricyclo[5.2.2.0$^{2,6}$]undec-4-yl, 4-endo-azatricyclo[5.2.2.0$^{2,6}$]undec-8-en-4-yl, 10-oxa-3-azatricyclo[5.2.1.0$^{1,5}$]dec-3-yl, and 10-methyl-3,10-diaza-tricyclo[5.2.1.0$^{1,5}$]dec-3-yl and also 3-hydroxy-8-azabicyclo[3.2.1]oct-8-yl (or notropinyl), the hydroxyl of which can be esterified by lower alkanoyl, carboxy-lower alkanoyl, di-lower alkylamino-lower alkanoyl, lower alkoxycarbonyl, which is unsubstituted or monosubstituted to trisubstituted by chlorine, or benzoyl, nictotinoyl, carbamoyl or toluene-sulphonyl or can be etherified by lower alkyl which is unsubstituted or monosubstituted to trisubstituted by lower alkoxy, carboxyl, the basic amino radicals defined above, especially di-lower alkylamino, or by phenyl or anisyl, the said azacyclic radicals being bonded via the aza ring nitrogen atom, and $R_2$ is carboxyl, acetyloxymethoxycarbonyl, methoxycarbonyloxymethoxycarbonyl, ethoxycarbonyloxymethoxycarbonyl, glycyloxymethoxycarbonyl, pivaloyloxymethoxycarbonyl, lower alkoxymethoxycarbonyl, especially methoxymethoxycarbonyl, or phthalidyloxycarbonyl, and also physiologically acceptable salts of such compounds.

The invention relates in particular to 6$\beta$-[(3-azabicyclo[3.2.2]non-3-yl)-methyleneamino]-penicillanic acid, 6$\beta$-[(4-azatricyclo[5.2.2.0$^{2,6}$]undec-4-yl)-methyleneamino]-penicillanic acid, 6$\beta$-[(4-endo-azatricyclo[5.2.2.0$^{2,6}$]undec-8-enyl)-methyleneamino]-penicillanic acid, 6$\beta$-[3-endo-hydroxy-8-aza-bicyclo[3.2.1]oct-8-yl)-methyleneamino]-penicillanic acid and 6$\beta$-[(7-methyl-3,7-diazabicyclo[3.3.1]non-3-yl)-methyleneamino]-penicillanic acid, and pivaloyloxymethyl 6β-[(4-endo-azatricyclo[5.2.2.0^{2,6}]undec-8-enyl)-methyleneamino]-penicillanate, as well as physiologically acceptable salts thereof.

The novel compounds of the formula I can be obtained by reacting a formamide or thioformamide, which can be activated, of the formula II

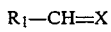     (II)

in which X is oxygen or sulphur and $R_1$ is as defined under formula I, and in which functional groups present in $R_1$ can be protected, or a reactive derivative of such a formamide or thioformamide, with a 6-aminopenam derivative of the formula III

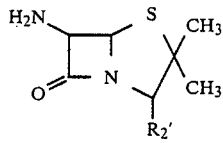     (III)

in which $R_2'$ has the meaning defined above for $R_2$ or is a protected carboxyl, or with a inorganic or organic salt of such a compound, and, if desired or necessary, in a resulting compound, converting a group $R_2'$ which differs from $R_2$ into a group $R_2$, and/or, if desired or necessary, detaching a protective group or groups present in one or more protected functional groups and/or, if desired or necessary, within the definition of the end products, converting a resulting compound into another compound and/or, if desired or necessary, converting a resulting compound of the formula I into a salt or converting a resulting salt into a compound of the formula I or into another salt, and/or, if desired or necessary, separating a resulting mixture of isomers into the individual isomers.

Preferred reactants for use with the 6-aminopenam derivatives of the formula III are the reactive derivatives of a formamide or thioformamide of the formula II which are defined below.

Reactive derivatives of the compounds of the general formula II are, for example, formiminium salts of the formula

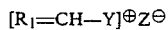     (IIa)

in which $R_1$ is as defined above and any free functional groups which may be present in $R_1$ preferably are temporarily protected, Y is halogen, especially chlorine, or a lower alkoxy which is unsubstituted or substituted by phenyl, lower alkoxy or halogen, such as chlorine, in particular methoxy, ethoxy or benzyloxy, and Z is halogen, such as chlorine, bromine or iodine, or the anionic radical of an alkylating agent, especially a monoalkylsulphate radical, such as a monomethyl-sulphate or monoethyl-sulphate radical, a dialkyl-phosphate radical, such as the dimethyl-phosphate radical, or the tetrafluoborate radical.

In a compound of the formula IIa, Y is in particular halogen, especially chlorine, and also lower alkoxy, especially methoxy or ethoxy, and Z is in particular halogen, especially chlorine, and also the metho- or etho-sulphate radical.

Preferred examples of starting compounds of the formula IIa are formiminium halides of the formula

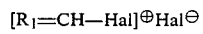

which can also be regarded as formamide dihalides of the formula $R_1$—CH(Hal)$_2$, and also alkylating agent adducts of the formula

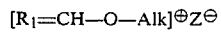

in which $R_1$ is as defined above and especially as defined above for preferred radicals $R_1$, Hal is halogen, especially chlorine, Alk is methoxy or ethoxy and Z is halogen, such as chlorine, bromine or iodine, and also the monomethyl-sulphate or monoethyl-sulphate radical.

Reactive derivatives of a formamide or thioformamide of the formula II are, for example, also formamide acetals or formamide thioacetals of the formula

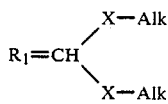     (IIb)

in which $R_1$ and X are as defined above and Alk is lower alkyl, which is unsubstituted or substituted by halogen, phenyl or lower alkoxy, especially methyl or ethyl.

In the compounds of the formula IIa or IIb any free functional groups which may be present in the radical $R_1$ can temporarily be protected, if necessary or desired.

The starting compounds of the formula III in which $R_2'$ is a free carboxyl group, an esterified carboxyl group splittable under physiological conditions or a protected carboxyl group are known and have been described, for example, in German Offenlegungsschriften Nos. 2,055,531, 2,123,111, 2,404,587 and 2,530,299 and also in Japanese Published Specification No. 039958/1976 (Derwent No. 89393 X/48).

The carboxyl, amino and hydroxyl protective groups which can be used in the starting compounds, for example those of the formulae IIa, IIb and III, are known and described in numerous patent specifications, for example in those mentioned above or in J. W. F. McOmie, "Protective Groups in Organic Chemistry", Plenum Press, New York, N.Y., 1973. Thus, examples of amino protective groups are given in chapter 2, of hydroxyl protective groups are given in chapter 3 and of carboxyl protective groups are given in chapter 5 of the last-mentioned publication.

Suitable protective groups of this type are also mentioned in E. Schröder and Lübke, "The Peptides", volume I, Academic Press, 1965, for example on pages 72–75.

A protected carboxyl group $R_2'$ in a starting material of the formula III is in particular an easily splittable esterified carboxyl group or a carboxyl group in the form of an anhydride.

An easily splittable esterified carboxyl group is, for example, a lower alkoxycarbonyl which is preferably substituted, in particular in the α-position or also in the β-position, and/or branched in the α-position. Substituents of such a group are, for example, carbocyclic aryl, such as phenyl, which is unsubstituted or substituted, for example by lower alkyl, such as tert.-butyl, phenyl, hydroxyl, lower alkoxy, such as methoxy, and/or nitro, aryloxy, such as phenyloxy which is unsubstituted or substituted, for example by lower alkoxy, such as methoxy, arylcarbonyl, such as benzoyl which is unsubstituted or substituted, for example by halogen, such as bromine, or cyano or acylamino, such as diacylamino, for example phthalimino or succinylimino; such substituents are preferably in the α-position of the lower alkoxycarbonyl group and, depending on the nature of the substituents, this group can contain one, two or more such radicals. Further substituents, which are preferably in the β-position of the lower alkoxycarbonyl group, are halogen, for example chlorine, bromine or iodine, and in such radicals an individual chlorine or bromine can easily be converted to iodine before setting free a carboxyl group protected in this way. Examples of suitable lower alkyl substituents in the abovementioned substituted or unsubstituted lower alkoxycarbonyl groups are tert.-lower alkyl, for example tert.-butyl, α-phenyl-lower alkyl which can be substituted in the phenyl radical, for example as indicated, such as benzyl, 4-methoxybenzyl or 4-nitrobenzyl, diphenylmethyl, which can be substituted in the phenyl radicals, for example as indicated, especially by lower alkoxy, for example methoxy, such as benzhydryl or 4,4'-dimethoxydiphenylmethyl, trityl, and also tris-(p-methoxyphenyl)-methyl, bis-phenyloxy-methyl, which can be substituted in the phenyl radicals, for example as indicated, especially by lower alkoxy, such as bis-(4-methoxyphenyloxy)methyl, phenacyl, which can be substituted, especially by halogen, such as phenacyl or 4-bromo-phenacyl, and also cyanomethyl, diacyliminomethyl, such as phthalyliminomethyl or succinyliminomethyl, or 2-halogeno-lower alkyl, such as 2,2,2-trichloroethyl, 2-bromoethyl or 2-iodoethyl.

Furthermore, an easily splittable esterified carboxyl group can also be a cycloalkoxycarbonyl group, in which the α-position is preferably a bridge head carbon atom. Corresponding cycloalkyl is, for example, 1-adamantyl.

Further protected carboxyl groups $R_2'$ are organic silyloxy- or stannyloxy-carbonyl radicals which carry 1 to 3 organic, especially aliphatic, hydrocarbon radicals, such as lower alkyl, for example methyl, ethyl, propyl or butyl or tert.-butyl, or halogeno-lower alkyl, for example chloromethyl or 2-chloroethyl, and also substituted or unsubstituted cycloaliphatic, aromatic or araliphatic hydrocarbon radicals, such as cycloalkyl, phenyl or phenyl-lower alkyl, and also etherified hydroxyl groups, for example lower alkoxy, such as methoxy or ethoxy, which, if desired, can contain halogen, such as chlorine, as further substituents. Preferred examples of such carboxyl protective groups are tri-lower alkylsilyl, for example trimethylsilyl or tert.-butyldimethylsilyl, tri-lower alkyl-silyl substituted by phenyl, for example trityl-dimethylsilyl, lower alkoxy-lower alkylhalogeno-silyl, for example chloro-methoxymethylsilyl, or tri-lower alkyl stannyl, for example tri-n-butyl-stannyl.

A protected carboxyl group $R_2'$ can also be a carboxyl esterified by a phenyl radical containing substituents providing a negative polarisation. Radicals providing a negative polarisation are halogen, especially chlorine, and nitro. A suitable radical of this type is the pentachlorophenyl protective group described in British Patent Specification No. 1,442,435.

A further suitably protected carboxyl is the β-silylethoxycarbonyl substituted by organic radicals, for example by the radicals mentioned above with regard to silyl protective groups, which is described in Belgian Patent Specification No. 851,576, especially β-trimethylsilylethoxycarbonyl.

A protected carboxyl group $R_2'$ which is in the form of an anhydride is preferably a free or esterified phosphoryloxycarbonyl group, for example a O,O'-diphenylphosphoryloxycarbonyl group, or a diphenylphosphinyloxycarbonyl group.

Preferred ester protective groups are those which can already be detached in the weakly acid to weakly basic range under conditions which are particularly gentle in respect of the penam ring structure, for example ester protective groups which are easily detachable by solvolylsis and are derived from tris-organosilyl alcohols, such as trimethylsilyl alcohol or β-trimethylsilylethanol. Such groups are described, for example, in British Patent Specification No. 1,073,530, in German Offenlegungsschrift No. 1,800,698 or in the abovementioned Belgian patent specification.

A carboxyl group which may be present in the radical $R_1$ can also be protected in the manner described above for $R_2'$ and specifically can be protected by the same or by another carboxyl protective group.

The primary amino group in a compound of the formula III and also a primary or secondary amino group which may be present in the radical $R_1$ of the compound of the formula IIa or IIb can also, if necessary, advantageously temporarily be protected by one of the amino protective groups known in peptide chemistry or in penicillin chemistry, preferably an easily detachable amino protective group. Such protective groups can be, for example, acyl, arylmethyl, 2-carbonyl-1-vinyl, arylthio, or aryl-lower alkylthio groups and also arylsulphonyl groups, as well as the organic silyl or stannyl groups mentioned above.

Amino groups protected in a particularly easily splittable form are amino groups acylated by a half-ester radical of carbonic or thiocarbonic acid, for example 2-iodoethoxycarbonyl (German Offenlegungsschrift No. 2,126,266), 6-nitroveratryloxycarbonyl and 2-nitrobenzyloxycarbonyl (J. Amer. Chem. Soc. 92, 6333 (1970)), 2-methylthioethoxycarbonyl (Chem. Ber. 109, 3693 (1976)) or tert.-butyloxycarbonyl, and also by 2-acyloxymethylbenzoyl, for example 2-benzoyloxymethylbenzoyl (J. Org. Chem. 41, 2029 (1976)) or by an aromatic phosphinic acid radical, for example diphenylphosphinyl (Tetrahedron Letters 1976, 3623)).

A hydroxyl group which may be present in a radical $R_1$ can also be in a temporarily protected form, especially in an easily splittable etherified or esterified form, for example in the form of a lower alkoxy group, such as a methoxy group, which is unsubstituted or substituted by lower alkoxy or lower alkylthio, for example in the form of a methoxymethoxy, methylthiomethoxy or β-methoxyethoxymethoxy group, or in the form of a 2-oxacycloalkoxy group, for example a 2-tetrahydropyranyloxy group, or of an acyloxy group, such as a lower alkanoyloxy group, for example an acetyloxy group, or in the form of an easily splittable etherified hydroxycarbonyloxy group, such as a lower alkoxycarbonyloxy group, for example a tert.-butyloxycarbonyloxy group.

The process used for the preparation of the compounds, according to the invention, of the formula I is known per se and is described in an analogous manner in German Offenlegungsschriften Nos. 2,055,531, 2,123,111, 2,404,587 and 2,530,299.

In this process, formamides or thioformamides, which can be activated, of the formula II, or reactive derivatives thereof, and the compound of the formula III are reacted with one another, preferably in the presence of an inert diluent, for example of an inert, preferably polar, solvent, and, if necessary, in the presence of further reaction-promoting additives, for example strong organic bases, condensing agents and/or catalysts, at reaction temperatures of between −80° and +80° C., preferably in the temperature range below +30° C. and especially with initial extensive cooling to temperatures below 0° C., if necessary in an inert gas atmosphere and in general with the exclusion of moisture.

When carrying out the process according to the invention, the reactive derivatives of a formamide or thioformamide of the formula II can be reacted with the penam compound of the formula III either after they have previously been isolated or after they have been formed in situ from their starting materials, without prior purification and/or isolation. Thus, for example, a formamide or thioformamide of the formula II can first be reacted with a halogenating agent, such as one of the halogenating agents mentioned below which can be used for the preparation of the halogenoformiminium halides of the formula IIa, especially phosgene or oxalyl chloride, if appropriate in the presence of a strong organic base, or can first be reacted with an active acetalising agent known per se, for example a reactive ortho-ester, such as one of the ortho-esters of formic acid mentioned below, a suitable ester of pentavalent phosphorus or a reactive amide acetal, preferably dimethylformamide dimethyl acetal, and the crude reaction mixture which contains the intermediates of the formula IIa or IIb and is formed as an intermediate can be allowed to react further, at the same time, subsequently or at a later time, in situ with an amine of the formula III, which can be protected, in a manner analogous to that employed when the compounds used have previously been isolated, the compounds, according to the invention, of the formula I being formed.

Finally, it is also possible to react a preferably equimolar mixture of the amines of the formula $R_1$—H and III, it being possible for the amino and/or carboxyl group in III and any free functional groups which may be present in $R_1$—H, with the exception of the azaamino group, temporarily to be protected, with a condensing agent which supplies the amidine carbon atom. Condensing agents which supply the amidine carbon atom are, in particular, reactive derivatives of orthoformic acid, for example orthoformates, especially aliphatic orthoformates, such as tri-lower alkyl orthoformates, corresponding thioorthoformates, di-lower alkylformamide diacetals and 1,1-dihalogenomethyl lower-alkyl ethers. Preferred derivatives of this type are trimethyl or triethyl orthoformates, trimethyl or triethyl thioorthoformates, dimethylformamide dimethylacetal and 1,1-dichlorodimethyl ether.

The process variant which proceeds via starting compounds of the formula IIa using 1,1-dichlorodimethyl ether as the condensing agent is advantageously carried out in the presence of a strong organic base and in an inert organic solvent; the process variant which proceeds via starting compounds of the formula IIb using orthoformates or thioorthoformates as the condensing agent preferably proceeds in the presence of an alkylating catalyst, such as a Lewis acid, for example zinc chloride or boron trifluoride etherate.

The reaction of a starting compound of the formula IIa, which has been isolated or has been prepared in situ, with a penam compound of the formula III is preferably carried out with temporary protection of the free functional groups and in the presence of a strong organic base. The imide halide of the formula IIa and the base are used, for example, in at least approximately equivalent amounts, but the latter can advantageously also be present in excess, for example in about twice to 3 times the equivalent amount. A further equivalent of the base must be used for each free carboxyl group which may be present in an intermediate. Suitable strong organic bases are, especially, the conventional acid-binding, salt-forming tertiary amines used in organic synthesis, for example tertiary aliphatic mono- or di-amines, such as tri-lower alkylamines, for example trimethylamine, triethylamine, tripropylamine or diisopropylethylamine, and also N,N,N',N'-tetra-lower alkyl-lower alkylenediamines, for example N,N,N',N'-tetraethylethylenediamine, cyclic mono-or di-amines, such as N-substituted, for example N-lower alkylated, alkyleneamines, azaalkyleneamines or oxaalkyleneamines, for example N-methylpiperidine or N-methylmorpholine; preferably suitable salt-forming tertiary amines are especially tri-lower alkylamines, for example triethylamine or diisopropylethylamine, and also N-methylmorpholine.

Suitable inert solvents or diluents are all absolute, preferably polar, solvents which do not possess any free functional groups. In particular, halogenated hydrocarbons, especially methylene chloride or chloroform, and also ketones, such as acetone, ethers, such as diethyl ether, anisole or tetrahydrofurane, and also aromatic hydrocarbons, for example benzene or toluene, or esters which are stable to hydrolysis, such as ethyl acetate, are suitable as the reaction medium.

In general, the starting compounds used in the above reaction are starting compounds of the formula IIa or IIb which have previously been isolated and are dissolved or suspended in one of the said inert solvents or diluents and are added to a solution of the compound of the formula III, the carboxyl group $R_2$ of which has previously been protected, for example by silylation, if starting materials of the formula IIa are used, after which the mixture is cooled to the said reaction temperature and the reaction is initiated or accelerated by adding the strong organic base.

In order to prepare the compounds of the formula I, it is also possible, as mentioned, to prepare the starting materials of the formula IIa in situ and to further use these direct, without prior purification or isolation. In this case, the same reaction conditions as mentioned above are maintained except that the reaction temperature is preferably chosen to be somewhat lower. Thus, for example, the reaction can be carried out at temperatures of initially −30° to −70°, after which the temperature is allowed to rise slowly.

The reaction of the starting compounds of the formula IIb with the compounds of the formula III is distinguished by the particular advantage that, with a procedure which in itself corresponds to that described above, a free carboxyl group in a compound of the formula III in general does not have to be protected and that the reaction also proceeds in an optimum manner from the start at somewhat higher temperatures, starting at about 0° and rising up to about +20° to +40° C.

In a compound of the formula I obtained by the process described, the carboxyl group $R_2$ and any functional group which may be present in the radical $R_1$ can also carry a protective group, which, if desired or necessary, can be detached in a manner known per se, for example by solvolysis, reduction or photolysis, or also enzymatically.

Thus, a silyl protective group used to protect a carboxyl, hydroxyl and/or amino group, for example the trimethylsilyl protective group, can be removed by solvolysis, for example by hydrolysis or alcoholysis, if this detaching has not already proceeded to completion during working up of the reaction mixture. A carboxyl group protected by a halogenolower alkyl group, especially a 2,2,2-trichloroethyl group, can be converted to the carboxylate, for example by treatment with a chemical reducing agent, such as a metal, for example zinc, or a reducing metal salt, for example chromium-II chloride or chromium-II acetate, usually in the presence of an acid, for example aqueous acetic acid or formic acid, or of a preferably aqueous alcohol, and a carboxyl group esterified by an arylcarbonylmethyl group can be converted to the carboxylate by treatment with a nucleophilic scission reagent, such as sodium thiophenolate or sodium iodide. A carboxyl group esterified by a suitable arylmethyl grouping can be split, for example, by irradiation, preferably with ultraviolet light, for example of less than 290 mµ, if the arylmethyl group is, for example, a benzyl radical which can be substituted in the 3-, 4- and/or 5-position, for example by lower alkoxy and-/or nitro groups, or with longer-wave ultraviolet light, for example of more than 290 mµ, if the arylmethyl group is, for example, a benzyl radical which is substituted in the 2-position by a nitro group. A carboxyl group esterified by a suitably substituted methyl group, such as tert.-butyl or diphenylmethyl, is set free in a particularly gentle manner, for example by treatment with a suitable acid agent, such as trifluoroacetic acid, if appropriate with the addition of a nucleophilic compound, such as phenol or anisole. An activated esterified carboxyl group or carboxyl group in the form of an anhydride can be split by hydrolysis with a neutral to weakly acid or weakly basic agent, which can contain water, such as acetic acid, aqueous sodium bicarbonate or an aqueous potassium phosphate buffer of pH about 7 to about 9, and an esterified carboxyl group which is splittable by hydrogenolysis, for example a carboxyl group esterified by benzyl, p-nitrobenzyl or p-methoxybenzyl, can be split preferably by hydrogenolysis, for example by treatment with hydrogen in the presence of a palladium catalyst.

A carboxyl or hydroxyl group protected by a benzyl protective group, which is unsubstituted or substituted, such as monosubstituted to polysubstituted by phenyl, methoxy or nitro, can be split, more or less readily, depending on the nature of the substituents, by the action of activated hydrogen or, if desired, by a weakly acid scission agent. Thus, the benzyl ester group or the p-methoxybenzyl ester group is split by the action of activated hydrogen in an inert, preferably alcoholic, solvent, such as a lower alkanol, for example ethanol, at normal or slightly elevated temperature, and the trityl ester group or the tris-(p-methoxyphenyl)-methyl ester group is already split by means of formic acid, which can contain water, for example at room temperature.

A carboxyl protected by a lower alkoxycarbonyl branched in the α-position, such as tert.-butoxycarbonyl, or by adamantyloxycarbonyl can likewise be set free by acidolysis, for example with lower alkanecarboxylic acids, for example acetic acid or formic acid.

In addition to the abovementioned weakly acid scission agents, further weak inorganic or organic acids or other weakly acid organic or inorganic compounds are also suitable as scission agents. Thus, polymers and adsorbents containing acid groups and also acids adsorbed on polymers are also suitable for this purpose; for example acid ion exchangers, acid adsorbents, such as silica gel or acid aluminium oxide, or insoluble or adsorbed phosphoric acids, for example metaphosphoric acids, or acid salts of phosphorus acids, and also Lewis acids in inert solvents are suitable as acidic scission agents.

A carboxyl group protected by an aryl radical containing substituents providing a negative polarisation, for example by pentachlorophenyl, can be freed from the protective radical by mild treatment with alkali, or with an organic base, for example those mentioned above.

A β-silylethyl protective group, for example a β-trimethylsilylethyl protective group, is split in a mild specific manner by a fluoride solution in organic media, for example KF in the presence of a crown ether, for example 18-crown ether-6, by tetraethylammonium fluoride or by HF-pyridine, preferably in an inert polar solvent, for example dimethylformamide.

Furthermore, one of the abovementioned physiologically splittable ester groups, for example a lower alkoxymethyl ester group, for example a methoxymethyl ester group, or a lower alkanoyloxymethyl ester group, for example a pivaloyloxymethyl ester group, can, if desired, also be detached in vitro, enzymatically or by one of the said scission agents, especially by a weakly acid scission agent, for example one of those mentioned above, and to this extent, if desired, can also be used for the temporary protection of the carboxyl group. Compounds containing the abovementioned, and especially the last-mentioned, physiologically splittable protective groups, in particular those containing a pivaloyloxymethyl ester group, are also readily convertible in vivo, into the corresponding free carboxylic acids of the formula I and are therefore preferably also suitable direct for use as antibacterial and/or antiviral active ingredients.

The hydroxyl protective groups corresponding to the carboxyl protective groups can also be removed in a manner known per se, for example in the manner described above.

Thus, for example, a methyl group substituted by aryl, such as trityl which is unsubstituted or substituted, such as substituted by methoxy, can be detached by the action of the abovementioned weakly acid agents, if desired in organic solvents, for example glacial acetic acid, or in a particularly gentle manner by treatment with acid ion exchangers or acid adsorbents such as silica gel or active aluminium oxide under mild conditions, for example by standing for several hours at room temperature. Preferred easily detachable hydroxyl protective groups are the trityl protective group and the tris-(p-methoxyphenyl)-methyl protective group.

Further hydroxyl protective groups which are particularly easily removable are derived from silyl alcohols. Thus, a trimethylsilyloxy group can already be detached, in a manner known per se, by aqueous lower alkanols, for example methanol, at normal or slightly elevated temperature.

A tetrahydropyranyl protective group, which is particularly preferred when the protective group has to withstand the action of basic or reducing agents, is also split easily in the presence of acid agents, for example those mentioned above.

Hydroxyl groups protected by etherification with lower alkoxy-lower alkyl can be split, for example, by treatment with zinc bromide or titanium tetrachloride in methylene chloride at room temperature and corresponding lower alkylthio-lower alkyl ethers can also be split by means of mercury-II chloride in aqueous acetonitrile or by means of methyl iodide and sodium carbonate in acetone at room temperature.

The amino protective groups corresponding to the said protective groups can be split in a similar manner, especially by hydrogenolysis or solvolysis, preferably acidolysis. Thus, for example, a lower alkoxycarbonyl protective group, which is preferably branched, for example the tert.-butoxycarbonyl group, can be detached in a manner known per se by treatment with acidic scission agents, for example those mentioned above, if desired in a preferably ethereal diluent, at or below room temperature.

A 2-(benzoyloxymethyl)-benzoylamino group can be split in weakly acid or alkaline solution and/or also by hydrogenolysis in the presence of a Pd/C catalyst, and a diphenylphosphorylamino group can be split in weakly acid trifluoroacetone.

Further amino protective groups which are also particularly easily detachable in another way are those described below. Thus, for example, the halogenoethoxycarbonyl protective group, especially the iodoethoxycarbonyl protective group, can be removed by the action of silver-I salts or mercury-I salts, such as corresponding nitrates, in an aqueous or organic medium, for example in acetone, and the methylthioethoxycarbonyl protective group, after methylation to dimethylsulphonioethoxycarbonyl or after oxidation to methylsulphinyl- or methylsulphonyl-ethoxycarbonyl, can be removed easily by mild treatment with alkali, and the 2,2'-dinitrodiphenylmethoxycarbonylamino, 6-nitroveratryloxycarbonylamino or 2'-nitrobenzyloxycarbonylamino group can be split quantitatively by the action of light having a wavelength of $>3,200$ Å.

If desired or necessary, it is possible, within the definition of the end products, to convert a resulting compound of the formula I into another compound of the formula I.

Thus, in a resulting compound of the formula I, a free or temporarily protected carboxyl group $R_2$ can be converted in a manner known per se into an esterified carboxyl group $R_2$ which is easily splittable under physiological conditions. The processes used for the subsequent esterification or transesterification are known.

The physiologically splittable esterified carboxyl groups $R_2$ can be prepared in a particularly simple manner from the corresponding carboxy compounds and the corresponding alcohol by a condensation reaction in the presence of a conventional condensing agent, such as of a carbodiimide, for example dicyclohexylcarbodiimide, or of a reactive N,N'-bis-heterocyclylurea, for example carbonyldiimidazole, for example in an inert polar solvent.

Furthermore, such esters are obtained, for example, by treatment with a suitable diazo compound, such as a diazo-lower alkane, for example diazomethane or diazobutane, or a phenyldiazo-lower alkane, for example diphenyldiazomethane, if necessary in the presence of a Lewis acid, for example boron trifluoride, or by reaction with an N,N'-disubstituted O- or S-substituted isourea or isothiourea in which a O- or S-substituent is, for example, lower alkyl, especially tert.-butyl, or phenyl-lower alkyl, and N- and N'-substituents are, for example, lower alkyl, especially isopropyl, cycloalkyl or phenyl, or by any other known and suitable esterification process, such as by reaction of a salt of the acid with a reactive ester of an alcohol and a strong inorganic acid or a strong organic sulphonic acid.

Furthermore, in a resulting compound of the formula I, a free or temporarily protected hydroxyl group present in the radical $R_1$ can be converted in a manner known per se to an esterified or etherified hydroxyl group defined according to the invention. Esterification reactions of this type can be carried out, for example, by reacting the hydroxy compound with the corresponding carboxylic or sulphonic acid in the presence of one of the abovementioned condensing agents, or by reacting the hydroxy compound with an isocyanate, acid anhydride or acid halide, if appropriate in the presence of the abovementioned bases, and corresponding etherification reactions can be carried out, for example, by using the conventional alkylating agents.

The said esterified or etherified hydroxyl groups, the lower alkyl substituent $X_1$ and/or the physiologically easily splittable esterified carboxyl group $R_2$ are preferably already present in this form in the starting materials, if they are adequately stable, i.e. do not change when the process according to the invention is carried out.

Salts of compounds of the formula I can be prepared in a manner known per se. Thus, salts of such compounds containing acid groups can be formed, for example, by treatment with metal compounds, such as alkali metal salts of suitable carboxylic acids, for example the sodium salt of α-ethylcaproic acid, or with a dilute alkali metal hydroxide, with ammonia or with a suitable organic amine, preferably stoichiometric amounts or only a small excess of the salt-forming agent being used. Acid addition salts of compounds of the formula I containing basic groupings are obtained in a conventional manner, for example by treatment with an acid or a suitable anion exchanger. Inner salts of compounds of the formula I which contain a salt-forming amino group and a free carboxyl group can be formed, for example, by neutralising salts, such as acid addition salts, to the isoelectric point, for example with weak bases, or by treatment with liquid ion exchangers.

Salts can be converted into the free compounds in a conventional manner, metal salts and ammonium salts being converted, for example, by treatment with suitable acids or cation exchangers and acid addition salts being converted by treatment with suitable basic agents or anion exchangers.

Resulting mixtures of isomers can be separated into the individual isomers by methods known per se; mixtures of diastereomers or stereoisomers, for example syn- and anti-isomers, can be separated, for example, by fractional crystallisation, adsorption chromatography (column chromatography or thin layer chromatography) or other known separating processes. Resulting racemates can be resolved into the antipodes in a conventional manner, if appropriate after introducing suitable salt-forming groupings, for example by forming a mixture of diastereoisomeric salts with optically active salt-forming agents, separating the mixture into the diastereoisomeric salts and converting the salts which have been separated off into the free compounds, or by fractional crystallisation from optically active solvents.

The process also comprises those embodiments in which compounds obtained as intermediates are used as starting materials and the remaining process steps are carried out with these, or the process is discontinued at any stage; furthermore, starting materials can be used in the form of derivatives or formed during the reaction.

Preferably, the starting materials used and the reaction conditions chosen are such that the compounds mentioned above as being particularly preferred are obtained.

Starting materials of the formula II in which the amino group can be substituted by a group which permits acylation are known or can be obtained according to known methods.

Thus, the compounds of the formula IIa in which Y and Z are halogen, especially chlorine, can be obtained by reacting an amine of the formula $R_1$—OH with a reactive derivative of formic acid, such as a 1,1-dihalogenomethyl alkyl ether, for example 1,1-dichlorodimethyl ether, or by using a formamide or thioformamide of the formula II as the starting compound and reacting this in a known manner with a halogenating agent, and either isolating the halogenoformiminium halide of the formula IIa, which is obtained in both cases, or using it further in situ.

Suitable halogenating agents are conventional halogenating agents, such as inorganic or organic acid halides, preferably those which decompose into reaction products which are volatile or can be separated off easily, especially corresponding chlorides, such as oxalyl chloride, phosgene, diphosgene (trichloromethyl chloroformate), phosphorus oxychloride, phosphorus pentachloride or thionyl chloride.

The reaction is in general carried out in an inert diluent or solvent, such as those mentioned above, especially in methylene chloride, chloroform, diethyl ether or toluene, at temperatures between $-10°$ and $+30°$ C. Compounds of the formula IIa in which Y is lower alkoxy, especially methoxy or ethoxy, and Z is the radical of an alkylating agent, especially halogen, the mono-lower alkyl-sulphate radical or tetrafluoborate, are obtained by reacting a formamide or thioformamide of the formula II with an alkylating agent. Suitable alkylating agents are conventional alkylating agents, for example lower alkyl halides, especially methyl iodide, di-lower alkylsulphates, for example dimethyl sulphate and diethyl sulphate, and also onium salts, for example of fluoboric acid or fluorosilicic acid, for example triethyloxonium tetrafluoborate. This reaction can be carried out in one of the inert solvents mentioned, at normal temperature or at temperatures up to the boiling point of the solvent.

The resulting iminium ether or iminium thioether salts of the formula IIa can be isolated and purified or, as described above, produced and used further in situ.

The formamide acetals and formamide thioacetals of the formula IIb can be obtained by allowing alcohols, such as lower alkanols, for example methanol or ethanol, to act on the iminium ether or iminium thioether salts described above, preferably in the presence of basic agents, for example the abovementioned tertiary amines or alcoholates, for example sodium methylate, or by treating an amine of the formula $R_1$—H with an activated or reactive derivative of orthoformic acid or thioorthoformic acid, such as an ester or amide acetal thereof, for example with an orthoester of formic acid or thioformic acid, preferably in the presence of Lewis catalysts, for example with trimethyl orthoformate or triethyl orthothioformate and $ZnCl_2$ or boron trifluoride etherate, or with a dimethylformamide diacetal, for example dimethylformamide dimethyl acetal, or by treating a formamide or thioformamide of the formula II in a manner known per se with an acetalising agent, such as a trialkyloxonium tetrafluoborate, for example triethyloxonium tetrafluoborate, and, if desired, subsequently treating the reaction product with an alkaline agent, for example with sodium methylate.

The reaction conditions are known and depend in particular on the vigour of the reaction to be expected. Thus, the reaction of an iminium ether salt with sodium methylate or an alcohol in the presence of a tertiary base is preferably carried out with cooling, for example at temperatures of about $-70°$ C. to about $+10°$ C., it being possible, however, also to carry out the reaction at higher temperatures, i.e. for example, of up to about $75°$ C., if the stability of the starting materials and of the reaction products permits a higher temperature.

The other reactions, for example, the reaction of dimethylformamide dimethyl acetal with an amine of the formula $R_1$—H, are preferably carried out in an inert solvent, or in an excess of the orthoformic acid derivative as a diluent, and, if desired, in order to accelerate the reaction, at the boiling point of this solvent or diluent.

The formamides or thioformamides of the formula II which can be used as starting materials can be obtained from the amines of the formula $R_1$—H using conventional formylating agents, for example chloral, for example by warming for several hours in an inert solvent, such as chloroform.

The amines of the formula $R_1$—H are known or can be prepared from known starting materials in a manner known per se or in an analogous manner.

In the process according to the invention and in any additional measures which may require to be carried out and also in the preparation of the starting materials it is possible, if necessary, temporarily to protect free functional groups, which do not participate in the reaction, in the starting materials or in the compounds obtainable according to the process, in a manner known per se, as described above, for example temporarily to protect free amino groups by acylation, tritylation or silylation, free hydroxyl or mercapto groups, for example, by etherification or esterification and free carboxyl groups, for example, by esterification, including silylation, and, in each case, after the reaction has taken place, to set these groups free, if desired, in a manner known per se, for example as described above, especially by solvolysis or reduction.

The pharmacologically acceptable compounds of the present invention can be used, for example, to prepare pharmaceutical preparations which contain an effective amount of the active substance or a mixture, such as one of the above-mentioned mixtures of active ingredients, together with or mixed with conventional inorganic or organic, solid or liquid, pharmaceutically acceptable carriers or adjuncts, and are suitable for enteral or, preferably, parenteral administration or, in the case of preparations for the treatment of infections of the respiratory passages, in particular also for topical application (for example in the form of nosedrops), administration by inhalation (for example in the form of an aerosol spray) or buccal administration (for example in the form of lozenges). Thus, tablets or gelatin capsules are used which contain the active ingredient together with adjuncts, such as carriers and fillers or diluents, for example sucrose, lactose, dextrose, mannitol, sorbitol, cellulose or cellulose derivatives, such as methylcellulose, calcium phosphates, for example tricalcium phosphate or calcium hydrogen phosphate and/or glycine, and lubricants, for example silicic acid, talc, stearic acid or salts thereof, such as magnesium stearate or calcium stearate, and/or polyethylene glycol; tablets also contain binders, for example magnesium aluminium silicate, starches, such as maize, corn, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. Furthermore, the novel pharmacologically active compounds can be used in the form of injectable preparations, for example preparations which can be administered intravenously, or of infusion, drip or inhalation solutions. Such solutions are preferably isotonic aqueous solutions or suspensions and these can, if desired, be prepared before use from lyophilised preparations which contain the active substance on its own, as a mixture or together with a carrier, for example mannitol. The pharmaceutical preparations can be sterilised and/or contain adjuncts, for example preservatives, stabilisers, wetting agents and/or emulsifiers, solubilising agents, salts for regulating the osmotic pressure and/or buffers. The pharmaceutical preparations of this specification which, if desired, can contain further pharmacological valuable substances are prepared in a manner known per se, for example by means of conventional mixing, granulating, sugar-coating, dissolving or lyophilising methods, and contain from about 0.1% to 100% and especially from about 1% to about 50% of the active ingredient, and lyophilisates contain up to approximately 100% of the active ingredient.

The following examples illustrate the invention; temperatures are in degrees Centigrade. The solvent used in thin layer chromatography is:
System A = isopropanol/formic acid/water (77:4:19) (silica gel is used as the carrier medium and ampicillin as the reference substance).

EXAMPLE 1

6$\beta$-[(3-Azabicyclo[3.3.2]non-3-yl)-methyleneamino]-penicillanic acid is obtained by adding 5 g of 6-aminopenicillanic acid all at once to a solution of 6.8 g of 3-dimethoxymethyl-3-azabicyclo[3.2.2]nonane and 4.3 ml of diisopropylethylamine in 100 ml of absolute methylene chloride, at 0°–5° under nitrogen as a blanketing gas, stirring the mixture at 0°–5° for about 10 minutes, stirring the resulting clear solution for a further 3 hours at room temperature, removing the solvent in vacuo, dissolving the residue, which has solidified as a foam, in 70 ml of acetone, whereupon crystallisation starts, after which the pH value of the solution is adjusted to 7.0 by means of toluene-4-sulphonic acid, and filtering off the crystals, washing them with acetone and recrystallising them from ethanol.

The compound is in the form of its inner salt; melting point 169°–170° (with decomposition); $[\alpha]_D^{20} = +281 \pm 1°$ (0.5N sodium bicarbonate); Rf 0.37 in system A (ampicillin=0.53); IR spectrum (in Nujol), bands at 5.62 (shoulder), 5.67, 5.97 and 6.28$\mu$.

The mono-hydrochloride of 6$\beta$-[(3-azabicyclo[3.2.2]-non-3-yl)-methyleneamino]-penicillanic acid is obtained as follows: 3.51 g (10 mmols) of the inner salt are dissolved in 50 ml of absolute chloroform, the equimolar amount of an approximately 5% strength solution of HCl in absolute ether is added and the crystalline product which precipitates on cooling and standing is filtered off with suction and washed several times with absolute ether.

3-Dimethoxymethyl-3-azabicyclo[3.2.2]nonane, which is used as the starting material, can be obtained as follows: 25 g of commercially available azabicyclononane and 25 ml of dimethylformamide dimethyl acetal are refluxed for 2 hours and volatile constituents are then distilled off under normal pressure until the temperature of the distillate is 60° and the remaining residue, which is a clear liquid, is distilled under N$_2$ under an oil pump vacuum. Boiling point$_{0.1}$ 70°.

EXAMPLE 2

6$\beta$-[(2-Azatricyclo[3.3.1.1$^{3,7}$]dec-2-yl)-methyleneamino]-penicillanic acid is obtained in the form of the monohydrate by reacting 5.4 g of 2-dimethoxymethyl-2-azatricyclo[3.3.1.1$^{3,7}$]decane and 3.9 ml of diisopropylethylamine with 4.6 g of 6-aminopenicillanic acid in the manner described in Example 1. The product which has crystallised out is washed with 1,4-dioxane and recrystallised from isopropanol. Melting point: 172°–174°; $[\alpha]_D^{20} = +236 \pm 1°$ (0.5N NaHCO$_3$); Rf 0.35 in system A (ampicillin=0.50); IR spectrum (in Nujol), bands at 5.65, 5.94, 6.16 and 6.26 (shoulder) $\mu$.

The 2-dimethoxymethyl-2-azatricyclo[3.3.1.1$^{3,7}$]decane used can be obtained analogously to Example 1, using 4.6 g of 2-azatricyclo[3.3.1.1$^{3,7}$]decane (H. Stetter and K. Heckel, Chem. Ber. 106, 339 (1973)) and 9.5 ml of dimethylformamide dimethyl acetal as the starting materials. Boiling point$_{0.1}$ 80°.

EXAMPLE 3

6$\beta$-[(3-Aza-10-oxatricyclo[5.2.1.0$^{1,5}$]dec-3-yl)-methyleneamino]-penicillanic acid is obtained in the form of the hemihydrate by reacting 2.1 g of 3-dimethoxymethyl-3-aza-10-oxatricyclo[5.2.1.0$^{1,5}$]decane and 1.41 ml of diisopropylethylamine with 1.65 g of 6-aminopenicillanic acid in the manner described in Example 1. The pH of the reaction solution is adjusted to 5.5–6.0 with toluene-4-sulphonic acid and the product which crystallises out is filtered off with suction and washed with a large amount of acetone. Melting point: 163° (with decomposition); $[\alpha]_D^{20} = +246 \pm 1°$ (0.5N NaHCO$_3$), Rf 0.25 in system A (ampicillin=0.55); IR spectrum (in Nujol), bands at 5.63 (shoulder), 5.67, 5.97 and 6.27$\mu$.

The starting material is obtained as follows:

(a) 16.6 g of potassium carbonate are added to 18.7 g of N-benzyl-2-furfurylamine (R. L. Hinmann and K. L. Hamm, J. Org. Chem. 23, 529 (1955)), dissolved in 120 ml of ethanol, 12.2 g of allyl bromide are then added dropwise at room temperature in the course of 15 minutes and the mixture is refluxed for 20 hours. After cooling, the mixture is filtered, the filtrate is evaporated in vacuo, the liquid residue is dissolved in 250 ml of ether, the solution is filtered to give a clear filtrate, the latter is washed twice with, in each case, 100 ml of water and dried over sodium sulphate and the ether is removed in vacuo and the residue is distilled. This gives [21.2 g=93.4%] N-allyl-N-benzyl-2-furfurylamine; boiling point$_{0.01}$82°–85°.

(b) 2.3 g of N-allyl-N-benzyl-2-furfurylamine are added to a solution of 1.4 g of oxalic acid dihydrate in 12 ml of water, the resulting white suspension is filtered and the clear filtrate is refluxed for 20 hours. N-benzyl-3-aza-10-oxatricyclo[2.1.0$^{1,5}$]dec-8-ene monooxalate, which precipitates in the form of slightly brownish coloured crystals on cooling, is filtered off with suction. Melting point: 195°–196°.

(c) 82.5 ml of ethanolic hydrochloric acid (4.88 g of HCl/100 ml) and 2. g of Pd/charcoal (containing 5% of Pd) are added to a solution of 22.7 g of the base, liberated from the above monooxalate, in 200 ml of absolute ethanol and the mixture is hydrogenated under 1–4 bars until 4.61 liters of hydrogen have been taken up, the catalyst is filtered off, the filtrate is concentrated to 50 ml in vacuo and about 30 ml of ether are added at about 40°. The crystals of 3-aza-10-oxatricyclo[5.2.1.0$^{1,5}$]decane hydrochloride which precipitate and have a melting point of 172°–173° are filtered off with suction and the base is liberated therefrom in the conventional manner.

(d) 3-Dimethoxymethyl-3-aza-10-oxa-tricyclo[5.2.1.0$^{1,5}$]decane is obtained analogously to Example 1, using 6.9 g (0.05 mol) of the above base and 15 ml (0.114 mol) of N,N-dimethylformamide dimethyl acetal as the starting materials; boiling point$_{0.1}$ 92°.

EXAMPLE 4

6β-[(4-Azatricyclo[5.2.2.0$^{2,6}$]undec-4-yl)-methyleneamino]-penicillanic acid is obtained in the form of the hemihydrate by reacting 9.2 g of 4-dimethoxymethyl-4-azatricyclo[5.2.2.0$^{2,6}$]undecane and 6 ml of diisopropylethylamine with 7.6 g of 6-aminopenicillanic acid in the manner described in Example 1. The pH of the reaction solution is adjusted to 5.5–6.0 with toluene-4-sulphonic acid and the product which crystallises out is filtered off with suction and washed with acetone. Melting point: 166° (with decomposition); $[\alpha]_D^{20} = 271 \pm 1°$ (0.5N NaHCO$_3$); Rf 0.36 in system A (ampicillin = 0.49); IR spectrum (in Nujol), bands at 5.65, 5.95 and 6.26μ.

The starting material 4-dimethoxymethyl-4-azatricyclo[5.2.2.0$^{2,6}$]undecane is obtained analogously to Example I using 9.1 g of 4-azatricyclo[5.2.2.0$^{2,6}$]undecane (M. Fumimoto and K. Okabe, Chem. Pharm. Bull. 10, 714 (1962)) and 20 ml of dimethylformamide dimethyl acetal as the starting materials; boiling point$_{0.9}$ 119°.

EXAMPLE 5

6β-[(4-endo-Azatricyclo[5.2.2.0$^{2,6}$]undec-8-enyl)methyleneamino]-penicillanic acid is obtained in the form of the hemihydrate by reacting 8.7 g of 4-dimethoxymethyl-4-endo-azatricyclo[5.2.2.0$^{2,6}$]undec-8-ene and 6 ml of diisopropylethylamine with 7.2 g of 6-aminopenicillanic acid in the manner described in Example 1, dissolving the evaporation residue in 80 ml of acetone, adjusting the pH of the solution to 5.5–6.0 with 5.6 g of toluene-4-sulphonic acid and filtering off, with suction, the crystals which precipitate, and washing them with acetone. Melting point: 166° (with decomposition); $[\alpha]_D^{20} = +262 \pm 1°$ (0.5N NaHCO$_3$); Rf 0.37 in system A (ampicillin = 0.49); IR spectrum (in Nujol), bands at 5.65, 5.95 and 6.26μ.

The starting material 4-dimethoxymethyl-4-endo-azatricyclo[5.2.2.0$^{2,6}$]undec-8-ene is obtained analogously to Example 1, using 10.8 g of 4-endo-azatricyclo[5.2.2.0$^{2,6}$]undec-8-ene (M. Fumimoto and K. Okabe, Chem. Pharm. Bull. 10, 714 (1962)) and 24 ml of dimethylformamide dimethyl acetal as the starting materials. Boiling point$_{0.9}$ 116°.

EXAMPLE 6

6β-[(3-endo-Benzhydryloxy-8-azabicyclo[3.2.1]oct-8-yl)-methyleneamino]-penicillanic acid is obtained by stirring a suspension of 1.3 g (6 mmols) of 6-aminopenicillanic acid in a solution of 2.4 ml (11.5 mmols) of hexamethyldisilazane and 50 ml of dry methylene chloride for 15 hours under reflux, cooling the resulting clear solution, adding 2.7 g (7.2 mmols) of 3-endo-benzhydryloxy-8-chloro-formiminium-8azabicyclo[3.2.1]octane chloride, dissolved in 20 ml of methylene chloride, stirring the mixture for a further one hour at room temperature, adding 15 ml of water dropwise, extracting the mixture three times with cold phosphate buffer of pH 7.8 and drying the organic layer over magnesium sulphate and evaporating it in vacuo. The residue is recrystallised from ether and then melts at 130° (with decomposition); $[\alpha]_D^{20} = 151 \pm 1°$ (1% in chloroform); Rf 0.63 in system A (ampicillin = 0.56); IR spectrum (in Nujol), bands at 5.67, 5.89 and 6.23μ.

The starting material can be obtained as follows:

(a) 3-Benzhydryloxynortropane hydrochloride (3.6 g; 0.9 mmol) (R. Banholzer, A. Heusner and W. Schulz, Annalen der Chemie 1975, 2227) is partitioned between 100 ml of 2N sodium hydroxide solution and 100 ml of chloroform, the chloroform solution is dried over magnesium sulphate and concentrated to 50 ml, 1.1 ml (11.5 mmols) of anhydrous chloral are added, the mixture is stirred overnight under reflux and evaporated, the residue is triturated with absolute ether, the material which is insoluble in ether is discarded, the clear ether solution is evaporated and the residue is recrystallised from cyclohexane. The resulting N-formyl-3-endo-benzhydryloxynortropane melts at 116°–118°.

(b) A solution of 0.72 ml (8.4 mmols) of oxalyl chloride in 5 ml of absolute ether is added dropwise to N-formyl-3-endo-benzhydryloxynortropane (2.6 g; 8.4 mmols) in 20 ml of absolute ether, at 0°–5°, with stirring, the resulting mixture is then stirred overnight at room temperature and the highly hygroscopic 3-endo-benzhydryloxy-8-chloro-formiminium-8-azabicyclo[3.2.1]octane chloride is dried over phosphorus-V oxide under a high vacuum.

EXAMPLE 7

6β-[(3-endo-Benzyloxy-8-azabicyclo[3.2.1]oct-8-yl)-methyleneamino]-penicillanic acid is obtained by stirring a suspension of 1.09 g (5 mmols) of 6-aminopenicillanic acid in a solution of 2 ml (10 mmols) of hexamethyldisilazane and 50 ml of dry methylene chloride for 15 hours under reflux, cooling the resulting clear solution, adding 1.7 g (5.7 mmols) of 3-endo-benzyloxy-8-chloro-formiminium-8-azabicyclo[3.2.1]octane chloride, dissolved in 20 ml of methylene chloride, stirring the reaction mixture for a further one hour at room temperature, adding 12 ml of water, extracting the mixture three times with cold phosphate buffer of pH 7.8 and drying the organic phase over anhydrous magnesium sulphate and evaporating it in vacuo. The residue, which has been triturated with absolute ether, melts at 128° (with decomposition), $[\alpha]_D^{20} = +216 \pm 1°$ (1% in chloroform); Rf 0.53 in system A (ampicillin = 0.56); IR spectrum (in Nujol); bands at 5.63, 5.82 and 6.26μ.

The starting material can be obtained as follows:

(a) 4.1 g of a dispersion of sodium hydride in oil (containing 60% of NaH) (0.102 mols of NaH) are introduced into a dry stirred flask, washed three times with dry pentane and covered with a layer of absolute dimethylformamide, a solution of 6.81 g (0.048 mol) of commercially available tropine in 100 ml of dimethylformamide is added, the mixture is warmed carefully to 75°, whereupon a vigorous evolution of hydrogen starts, and is then stirred for a further 1 hour at 75° and cooled to room temperature, 8.24 ml (0.07 mol) of benzyl bromide in 50 ml of dimethylformamide are added dropwise, with vigorous stirring, the mixture is stirred overnight at 80° and evaporated in a rotary evaporator, the resinous residue is dried under a high vacuum at 0.1 mm Hg and partitioned between 2N HBr and methylene chloride and the organic phase is washed twice with water, dried over magnesium sulphate and evaporated and this gives a brownish residue which, when recrystallised from acetone, gives 3-endo-benzyloxy-8-methyl-8-azabicyclo[3.2.1]octane hydrobromide with a melting point of 202°–204°.

(b) The base liberated from the above hydrobromide is dissolved in 16 ml of absolute toluene, 30 ml of phosgene in toluene (20% strength) are added and the mixture is stirred for 3 days at room temperature. A small amount of material which has precipitated is filtered off and the clear filtrate is evaporated completely, whereupon 3-endo-benzyloxy-8-chloroformyl-8-azabicyclo[3.2.1]octane is obtained in the form of a clear, virtually colourless oil.

(c) The above intermediate (1.6 g=0.034 mol) is suspended in 500 ml of water in a 2 liter stirred flask, the suspension is stirred under reflux for 30 minutes and filtered hot and the clear solution is evaporated completely, whereupon colourless crystals are obtained which, when recrystallised from isopropanol, give 3-endo-benzyloxynortropane hydrochloride with a melting point of 223°–225°.

(d) 1.07 ml (1.2 mmols) of anhydrous chloral are added to the base (2.4 g=11 mmols) liberated from the above hydrochloride, in 40 ml of chloroform, the mixture is stirred overnight under reflux and evaporated and the resulting colourless oil is dissolved in methylene chloride, the solution is filtered through 100 g of silica gel and the filtrate is evaporated, whereupon N-formyl-3-endo-benzyloxynortropane is obtained in the form of a colourless oil.

(e) 3-endo-Benzoyloxy-8-chloro-formiminium-8-azabicyclo[3.2.1]octane chloride is obtained analogously to Example 6(b) from 1.9 g (7.75 mmoles) of N-formyl-3-endo-benzyloxynortropane.

EXAMPLE 8

8.4 ml (60 mmols) of triethylamine and then 6.6 g (20 mmols) of 3-endo-(N,N-dimethylaminoacetoxy)-8-chloroformiminium-8-azabicyclo[3.2.1]octane chloride in 20 ml of methylene chloride are added to 50 ml of an ice-cold solution of trimethylsilyl 6-amino-penicillanate in methylene chloride, prepared analogously to Example 7 from 4.32 g (20 mmols) of 6-aminopenicillanic acid. The mixture is stirred for 1 hour at room temperature and poured into 100 ml of ice-cold phosphate buffer solution of pH 7.8, the organic phase is separated off, dried over MgSO4 and evaporated in vacuo and the residue is triturated with diethyl ether, whereupon 6β-[(3-endo-(N,N-dimethylaminoacetoxy)-8-azabicyclo[3.2.1]oct-8-yl)-methyleneamino]-penicillanic acid is obtained in crystalline form.

The starting material is prepared as follows:

(a) 6.05 g (41 mmols) of chloral are added to 5.2 g (41 mmols) of nortropine [S. P. Findlay, J. Amer. Chem. Soc. 75, 3204 (1953)] in 100 ml of chloroform and the mixture is stirred overnight at 50°. It is evaporated in vacuo and the residue is stirred with 20 ml of anhydrous diethyl ether, whereupon N-formylnortropine with a melting point of 105°–110° is obtained.

(b) 5.5 ml (32 mmols) of diisopropylethylamine are added to 5 g (32 mmols) of N-formylnortropine in 100 ml of absolute benzene and the mixture is cooled to 0°–5°. A solution of 2.6 ml (32 mmols) of chloroacetyl chloride in 50 ml of benzene is added dropwise to this mixture at 0°–5° and the resulting mixture is then stirred for 20 hours at room temperature. The mixture is extracted with water and the organic phase is dried over MgSO4 and evaporated in vacuo. The residue is extracted with diethyl ether and the ether extract is filtered through about 50 g of silica gel and evaporated, whereupon 3-endo-chloroacetyloxy-8-formyl-8-azabicyclo[3.2.1]octane is obtained in the form of light brown oil.

(c) 2.3 g (10 mmols) of the above chloroacetyloxy compound and 2.5 ml of a solution of dimethylamine in benzene (20% strength) are warmed at 80° in a bomb tube overnight. The mixture is evaporated completely in vacuo and the residue is partitioned between 50 ml of ice-cold phosphate buffer solution of pH 7.4 and 50 ml of methylene chloride. The organic phase is dried and evaporated in vacuo, whereupon 3-endo-(N,N-dimethylaminoacetoxy)-8-formyl-8-azabicyclo[3.2.1]octane is obtained.

(d) A solution of 0.86 ml (10 mmols) of oxalyl chloride in 5 ml of diethyl ether is added dropwise at 0°–5° to 2.4 g (10 mmols) of the above compound in 40 ml of absolute diethyl ether and the mixture is then stirred overnight at room temperature. 3-endo-(N,N-Dimethylaminoacetoxy)-8-chloroformiminium-8-azabicyclo[3.2.1]octane chloride, which has precipitated, is highly hygroscopic and is therefore employed after drying briefly over phosphorus-V oxide under a high vacuum, without further purification.

EXAMPLE 9

Analogously to Example 8, 6β-[(3-endo-(2-benzyloxycarbonylacetyloxy)-8-azabicyclo[3.2.1]oct-8-yl)-methyleneamino]-penicillanic acid is obtained from 4.32 g (20 mmols) of 6-aninopencillanic acid and 7.48 g (20 mmols) of 3-endo-(2-benzyloxycarbonylacetyloxy)-8-chloroformiminium-8-azabicyclo[3.2.1]octane chloride in the presence of 5.6 ml (40 mmols) of triethylamine and is hydrogenated with palladium-on-charcoal (10% of Pd) in methanol under normal pressure. The catalyst is filtered off, the filtrate is evaporated in vacuo and the residue is crystallised from diethyl ether, whereupon 6β-[(3-endo-malonyloxy-8-azabicyclo[3.2.1]oct-8-yl)-methyleneamino]-penicillanic acid is obtained.

(a) The starting material required for this reaction is obtained by adding a solution of 7.1 g (33.6 mmols) of benzylmalonic acid chloride in 50 ml of benzene to 5 g (32 mmols) of the N-formylnortropine, described in Example 8, in 200 ml of absolute benzene in the presence of 4.9 g (38 mmols) of diisopropylethylamine, at 0°–5°, and then stirring the mixture overnight at room temperature. The resulting 3-endo-(2-benzyloxycarbonylacetyloxy)-8-formyl-8-azabicyclo[3.2.1]octane is isolated in the form of a brown oil by pouring the solution on to dilute sodium bicarbonate solution and ice and separating off the organic phase, drying it over MgSO4 and evaporating it. For further purification, the crude material is chromatographed on 200 g of silica gel and this gives a virtually colourless oil (6.6 g=20 mmols).

(b) Analogously to the method described in Example 8, 3-endo-(2-benzyloxycarbonylacetyloxy)-8-chloroformiminium-8-azabicyclo[3.2.1]octane chloride is obtained from 6.6 g (20 mmols) of the above product, by reacting it with 1.72 ml (20 mmols) of oxalyl chloride.

EXAMPLE 10

Analogously to the method described in Example 8, pure 6β-[(3-endo-(2-dimethylaminoethoxy)-8-azabicyclo[3.2.1]oct-8-yl)-methyleneamino]-penicillanic acid is obtained from 4.32 g (20 mmols) of 6-aminopenicillanic acid and 5.44 g (20 mmols) of 3-endo-(2-dimethylaminoethoxy)-8-chloroformiminium-8-azabicyclo[3.2.1]octane chloride in the presence of 5.6 g (40 mmols) of triethylamine.

The starting material is prepared as follows:

(a) 0.5 g of tetrabutylammonium bisulphate, 80 ml of toluene and 2.5 g (21 mmols) of 2-dimethylaminoethyl chloride are added to 15 ml of 50% strength sodium hydroxide solution. 3.1 g (20 mmols) of N-formylnortropine are added in portions to this mixture in the course of 1 hour, at room temperature, with stirring, and the mixture is then stirred for a further 1 hour. The organic phase is separated off, twice extracted by shaking with, in each case, 100 ml of water, dried over $MgSO_4$ and evaporated in vacuo. The crude 3-endo-(2-dimethylaminoethoxy)-8-formyl-8-azabicyclo[3.2.1]octane obtained in this way is reacted analogously to the method described in Example 9(b) with 1.72 ml (20 mmols) of oxalyl chloride and this gives 3-endo-(2-dimethylaminoethoxy)-8-chloroformiminium-8-azabicyclo[3.2.1]octane chloride, which is dried over phosphorus-V oxide under a high vacuum.

EXAMPLE 11

Phosgene is passed, at 0°-5°, into a solution of 3.82 g (0.0115 mols) of 3-endo-trichloroethoxycarbonyloxy-8-formyl-8-azabicyclo[3.2.1]octane in 150 ml of diethyl ether, in an apparatus dried under nitrogen, until no further precipitate forms. The 3-endo-trichloroethoxycarbonyloxy-8-chloroformiminium-8-azabicyclo[3.2.1]octane chloride prepared in this way is filtered off under nitrogen and dissolved in 50 ml of chloroform and this solution is added dropwise at 0°-5° in the course of 30 minutes to a solution of trimethylsilyl 6-aminopenicillanate, prepared from 2.16 g (0.01 mol) of 6-aminopenicillanic acid and hexamethyldisilazane in 100 ml of chloroform [K. W. Glombitza, Annalen der Chemie 673, 166 (1964)]. The mixture is cooled to −10° to −15° and 3.75 ml of triethylamine are added dropwise at this temperature, whereupon a slight red coloration develops. After a further 30 minutes at this temperature, the mixture is evaporated completely at 0° and the residual solid foam is triturated with a solution of 0.5 ml of 2-butanol in 100 ml of diethyl ether. The virtually colourless powder is filtered off and dried over $P_2O_5$ in vacuo. 4.1 g of 6β-[(3-endo-trichloroethoxycarbonyloxy-8-azabicyclo[3.2.1]oct-8-yl)-methyleneamino]-penicillanic acid with a melting point of 138° (with decomposition) are obtained in this way.

The starting material is prepared as follows:

(a) 6.05 g (0.04 mol) of chloral are added to 5.2 g (0.041 mol) of nortropine in 100 ml of chloroform and the mixture is stirred for 16 hours at 50°. It is evaporated in vacuo and the residue is stirred with 20 ml of anhydrous diethyl ether, whereupon 4.4 g of N-formylnortropine with a melting point of 105°-110° are obtained.

(b) 11 ml (0.081 mol) of trichloroethyl chloroformate are added, at 0.5°, to 12.7 g (0.081 mol) of N-formylnortropine in 310 ml of anhydrous tetrahydrofurane. 6.6 ml (0.081 mol) of pyridine are then added dropwise in the course of 1 hour, with stirring, and the mixture is stirred for a further 1 hour at this temperature and then filtered and the filtrate is evaporated in vacuo. The residue is partitioned between water and methylene chloride and the organic phase is separated off and washed twice with water. Drying over sodium sulphate and evaporating in vacuo gives a colourless oil, which crystallises on the addition of 50 ml of diethyl ether. 11.1 g of 3-endo-trichloroethoxycarbonyloxy-8-formyl-8-azabicyclo[3.2.1]octane with a melting point of 115°-116° are obtained in this way.

EXAMPLE 12

500 mg (0.001 mol) of 6β-[(3-endo-trichloroethoxycarbonyloxy-8-azabicyclo[3.2.1]oct-8-yl)-methyleneamino]-penicillanic acid are dissolved in a mixture of 5 ml of glacial acetic acid and 5 ml of acetonitrile, and 650 mg (0.01 gram atom) of zinc powder are added to this solution at 0°-5°, the addition being made in 100 mg portions in the course of 6 hours. The subsequent operations have to be carried out at 0°-5°:

The excess zinc is filtered off and the filtrate is evaporated under a high vacuum. The yellow resinous residue is dissolved in 20 ml of water and hydrogen sulphide is passed into the mixture until no further precipitate forms. The mixture is filtered and the filtrate is extracted with three 50 ml portions of methylene chloride. Lyophilisation of the aqueous phase gives 135 mg of 6β-[(3-endo-hydroxy-8-azabicyclo[3.2.1]oct-8-yl)-methyleneamino]-penicillanic acid.

EXAMPLE 13

551 mg (0.00328 mol) of N-formyl-N'-methylbispidine (=3-formyl-7-methyl-3,7-diazabicyclo[3.2.1]nonane) are dissolved in 20 ml of diethyl ether, in an apparatus dried under nitrogen, and phosgene is passed into this solution at 0°-5° until no further precipitate forms. The N-chloroformiminium-N'-methylbispidine chloride prepared in this way is filtered off under nitrogen and dissolved in 5 ml of chloroform and this solution is added dropwise at 0°-5° in the course of 15 minutes to a solution of trimethylsilyl 6-aminopenicillanate, prepared from 648 mg (3.0 mmols) of 6-aminopenicillanic acid and hexamethyldisilazane in 20 ml of chloroform [K. W. Glombitza, Annalen der Chemie 673, 166 (1964)]. The mixture is stirred for a further 9 hours at this temperature and evaporated in vacuo. The resinous residue is stirred with a mixture of 0.2 ml of 2-butanol in 20 ml of diethyl ether and 909 mg of 6β-[(7-methyl-3,7-diazabicyclo[3.3.1]non-3-yl)-methyleneamino]-penicillanic acid with a melting point of 160° (with decomposition) are obtained.

The starting material is prepared as follows:

0.527 g of chloral is added to 0.5 g (0.00358 mol) of N-methylbispidine [E. E. Smissman & P. C. Ruenitz, J. org. Chem. 41, 1593 (1976)] dissolved in 10 ml of chloroform and the mixture is warmed at 50° for 15 hours. The cooled mixture is allowed to run through a 2 cm high column (diameter 2 cm) containing aluminium oxide and the column is rinsed with 50 ml of chloroform. After evaporating in vacuo, 551 mg of N-formyl-N'-methylbispidine are obtained and this is used without further purification.

EXAMPLE 14

Pivaloyloxymethyl 6β-[(4-endo-azatricyclo[5.2.2.0$^{2,6}$]undec-8-enyl)-methyleneamino]-penicillanate is obtained by stirring 5.0 g (0.013 mol) of 6β-[(4-endo-azatricyclo[5.2.2.0$^{2,6}$]undec-8-enyl)-methyleneamino]-penicillanic acid (corresponding to Example 5) and 2 ml (0.015 mol) of triethylamine in 40 ml of dimethylformamide until a virtually clear solution forms, adding 1.95 g (0.013 mol) of pivaloyloxymethyl chloride all at once and stirring the mixture further overnight at room temperature, under nitrogen as a blanketing gas, removing the solvent in vacuo, stirring up the residue in ethyl acetate, filtering the resulting suspension, extracting the filtrate twice with ice-cooled saturated sodium bicarbonate solution and once with ice-water, drying it over magnesium sulphate and evaporating and recrystallising the residue, which has solidified as a foam, from 20 ml of diethyl ether; melting point 177°–178°; $[\alpha]_D^{20}$ 432±1° (1.0% in CHCl$_3$); IR spectrum (in CH$_2$Cl$_2$), bands at 1760, 1650 and 1608 cm$^{-1}$.

For conversion to the hydrochloride, the above compound is dissolved in methylene chloride, the calculated amount of an ethereal solution of HCl is added and the hydrochloride is made to crystallise by adding further ether and is dried. White crystals with a melting point of 142° (with decomposition).

EXAMPLE 15

Dry ampoules or phials containing 0.5 g of the inner salt of 6β-[(3-azabicyclo[3.2.2]non-3-yl)-methyleneamino]-penicillanic acid are prepared as follows:
Composition (for 1 ampoule or phial):
  Inner salt of 6β-[(3-azabicyclo[3.2.2]non-3-yl)-methyleneamino]-penicillanic acid: 0.5 g
  Mannitol: 0.05 g A sterile aqueous solution of the inner salt of 6β-[(3-azabicyclo[3.2.2]non-3-yl)-methyleneamino]-penicillanic acid and of the mannitol is subjected to freeze-drying under aseptic conditions in 5 ml ampoules or 5 ml phials and the ampoules or phials are sealed and checked.

Dry ampoules containing the other active ingredients of the formula I described in the above examples, for example containing 6β-[(4-azatricyclo[5.2.2.0$^{2,6}$]undec-4-yl)-methyleneamino]-penicillanic acid, 6β-[(endo-azatricyclo[5.2.2.0$^{2,6}$]undec-8-enyl)-methyleneamino]-penicillanic acid or pivaloyloxymethyl 6β-[(endo-azatricyclo[5.2.2.0$^{2,6}$]undec-8-enyl)-methyleneamino]-penicillanate, or a hydrate or pharmaceutically acceptable salt of these compounds, can be obtained in an analogous manner.

EXAMPLE 16

Capsules containing 0.25 g of the inner salt of 6β-[(3-azabicyclo[3.2.2]non-3-yl)-methyleneamino]-penicillanic acid are prepared as follows:
Composition (for 1,000 capsules):
  Inner salt of 6β-[(3-azabicyclo[3.2.2]non-3-yl)-methyleneamino]-penicillanic acid: 250.000 g
  Maize starch: 50.000 g
  Polyvinylpyrrolidone: 15.000 g
  Magnesium stearate: 5.000 g
  Ethanol: q.s.

The inner salt of 6β-[(3-azabicyclo[3.2.2]non-3-yl)-methyleneamino]-penicillanic acid and the maize starch are mixed and the mixture is moistened with a solution of the polyvinylpyrrolidone in 50 g of ethanol. The moist mass is pressed through a sieve with a mesh width of 3 mm and dried at 45°. The dry granules are forced through a sieve with a mesh width of 1 mm and mixed with 5 g of magnesium stearate. The mixture is filled, in 0.320 g portions, into hard gelatin capsules.

Capsules containing other active ingredients of the formula I described in the above examples, for example containing 6β-[(2-azatricyclo[3.3.1.1$^{3,7}$]dec-2-yl)-methyleneamino]-penicillanic acid monohydrate and 6β-[(3-endo-hydroxy-8-azabicyclo[3.2.1]oct-8-yl)-methyleneamino]-penicillanic acid, 6β-[(4-azatricyclo[5.2.2.0$^{2,6}$]undec-4-yl)-methyleneamino]-penicillanic acid, 6β-[(endo-azatricyclo[5.2.2.0$^{2,6}$]undec-8-enyl)-methyleneamino]-penicillanic acid or pivaloyloxymethyl 6β-[(endo-azatricyclo[5.2.2.0$^{2,6}$]undec-8-enyl)-methyleneamino]-penicillanate, can be obtained in an analogous manner.

EXAMPLE 17

Capsules which each contain 0.200 g of the hydrochloride of pivaloyloxymethyl 6β-[(endo-azatricyclo[5.2.2.0$^{2,6}$]undec-8-enyl)-methyleneamino]-penicillanate and 0.04 g of trimethoprim are prepared by the following procedure:
Constituents:
  The hydrochloride of pivaloyloxymethyl 6β-[(endo-azatricyclo[5.2.2.0$^{2,6}$]undec-8-enyl)-methyleneamino]-penicillanate: 200 g
  Trimethoprim: 40 g
  Polyvinylpyrrolidone: 10 g
  Magnesium stearate: 4 g The hydrochloride of pivaloyloxymethyl 6β-[(endo-azatricyclo[5.2.2.0$^{2,6}$]undec-8-enyl)-methyleneamino]-penicillanate and the trimethoprim are mixed and the mixture is passed through a 0.84 mm sieve (20 U.S. Standard mesh). After mixing again, the resulting powder is moistened with a solution of polyvinylpyrrolidone in 150 ml of isopropanol. The moistened mixture is granulated by passing it through a 0.84 mm sieve (20 U.S. Standard mesh) and is then dried at 30° C. A conventional drying oven with compartments or another suitable drying apparatus, which operates, for example, on the fluid bed principle, can be used for the drying operation.

After drying, the granules are passed through a 0.70 mm sieve (25 U.S. Standard mesh) and finally mixed with the magnesium stearate.

The granules, which are now ready to use, are filled into No. 1 hard gelatin capsules, each capsule containing about 0.260 g of granules comprising the above constituents; this corresponds to about 1,000 capsules.

EXAMPLE 18

Tablets which each contain 0.200 g of the hydrochloride of pivaloyloxymethyl 6β-[(endo-azatricyclo[5.2.2.0$^{2,6}$]undec-8-enyl)-methyleneamino]-penicillanate and 0.020 g of trimethoprim are prepared by the following procedure:
Constituents:
  The hydrochloride of pivaloyloxymethyl 6β-[(endo-azatricyclo[5.2.2.0$^{2,6}$]undec-8-enyl)-methyleneamino]penicillanate: 200 g
  Trimethoprim: 20 g
  Polyvinylpyrrolidone: 10 g
  Microcrystalline cellulose: 175 g
  Starch: 80 g
  Magnesium stearate: 4 g The hydrochloride of pivaloyloxymethyl 6β-[(endo-azatricyclo[5.2.2.0$^{2,6}$]undec-8-enyl)-methyleneamino]-penicillanate and the trimethoprim are mixed and sieved as indicated in Example 17. After mixing again, the resulting powder is moistened with 100 ml of a solution of polyvinylpyrrolidone in isopropanol. The moistened mixture is granulated by sieving it through a 0.84 mm sieve (20 U.S. Standard mesh) and is then dried at 30° C. After drying, the granules are passed through a 0.70 mm sieve (25 U.S. Standard mesh) and are then mixed with the microcrystalline cellulose, the starch and the magnesium stearate. Using presses with a diameter of 12 mm, the granules are compressed to tablets which each contain about 0.500 g of the above constituents; this corresponds to 1,000 tablets.

EXAMPLE 19

Following the procedure described in Example 17, a tablet is prepared which has the following composition:
Constituents for 1,000 tablets:
  Pivaloyloxymethyl 6β-[(endo-azatricyclo[5.2.2.0$^{2,6}$]undec-8-enyl)-methyleneamino]-penicillanate: 250 g
  Trimethoprim: 100 g
  Polyvinylpyrrolidone: 10 g
  Microcrystalline cellulose: 175 g
  Starch: 80 g
  Magnesium stearate: 5 g
  Each tablet weighs about 0.625 g

EXAMPLE 20

The following mixture is prepared for peroral administration, which can be used in particular for the treatment of infections of the respiratory passages; this mixture is intended for preparation in the form of a suspension in water or in another potable liquid immediately before use. The mixture consists of the dose of the following constituents:
  Pivaloyloxymethyl 6β-[(endo-azatricyclo[5.2.2.0$^{2,6}$]undec-8-enyl)-methyleneamino]-penicillanate: 100 mg
  Trimethoprim: 20 mg
  Methylcellulose: 10 mg
  Sugar: 2.5 mg
  Saccharin sodium: 2.5 mg
  Aroma, as desired: 8 mg This dose is intended for suspension in approximately 5 ml of a suitable liquid.

In Examples 19–20, it is also possible to use, in place of the pivaloyloxymethyl ester, the hydrochloride of pivaloyloxymethyl 6β-[(endo-azatricyclo[5.2.2.0$^{2,6}$]undec-8-enyl)-methyleneamino]-penicillanate or one of the other compounds mentioned in Examples 15 and 16, or a salt thereof.

What is claimed is:

1. A 6-amino-penam compound of the formula

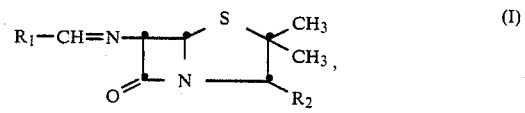

wherein R$_1$ is azabicycloalkyl, azatricycloalkyl, azabicycloalkenyl, oxaazabicycloalkyl, diazabicycloalkyl, azatricycloalkenyl, oxaazatricycloalkyl or diazatricycloalkyl, which is bonded via a ring nitrogen atom and has 1-3 endo bridge atoms, and contains a total of 7 to 12 ring atoms, wherein a ring carbon atom is unsubstituted or substituted by hydroxy, hydroxyl esterified by lower alkanoyl, carboxyl-lower alkanoyl, di-lower alkylamino-lower alkanoyl, lower alkoxycarbonyl, lower alkoxycarbonyl monosubstituted to trisubstituted by chlorine, or benzoyl, nicotinoyl, carbamoyl or toluene-sulfonyl, or hydroxyl etherified by lower alkyl, lower alkyl monosubstituted to trisubstituted by lower alkoxy, carboxyl, di-lower alkylamino, phenyl or anisyl, wherein a second nitrogen atom is substituted by hydrogen or lower alkyl, R$_2$ is free carboxyl or carboxyl esterified by a conventional physiologically detachable group, or a pharmaceutically acceptable salt of said compound.

2. A 6-amino-penam compound of the formula I according to claim 1, in which R$_1$ is 8-azabicyclo[3,2.1]oct-8-yl, 2-azabicyclo[2.2.2]oct-2-yl, 3-azabicyclo[3.2.2.]non-3-yl, 9-azabicyclo[3.3.1]non-9-yl, 3,7-diazabicyclo[3.3.1]non-3-yl, 9-azabicyclo[3.3.1]non-9-yl, 3.7-diazabicyclo[3.3.1]non-3-yl, 2-azatricyclo[3.3.1.1$^{3,7}$]dec-2-yl, 4-azatricyclo[5.2.1.0$^{2,6}$]dec-4-yl, 3-azatricyuclo[5.2.1.0$^{1,5}$]dec-3-yl, 4-azatricyclo[5.2.2.0$^{2,6}$]undec-4-yl, 8-azatricyclo[4.3.2.0$^{1,6}$]undec-8-yl, 4-azatricyclo[5.2.1.0$^{2,6}$]dec-8-en-4-yl, 4-azatricyclo[5.2.2.0$^{2,6}$]undec-8-en-4-yl, 8-azatricyclo[4.3.2.0$^{1,6}$]undec-3-en-8-yl, 10-oxa-3-azatricyclo[5.2.1.0$^{1,5}$]dec-3-yl, 10-oxa-4-azatricyclo[5.2.1.0$^{2,6}$]dec-4-yl, 3,10-diazatricyclo[5.2.1.0$^{1,5}$]dec-3-yl, 3-endo-hydroxy-8-azabicyclo[3.2.1.]oct-8-yl, the hydroxyl group of which is free, esterified by lower alkanoyl, carboxyl-lower alkanoyl, di-lower alkylamino-lower alkanoyl, lower alkoxycarbonyl, lower alkoxycarbonyl monosubstituted to trisubstituted by chlorine, or benzoyl, nicotinoyl, carbamoyl, or toluene-sulfonyl or hydroxyl etherified by lower alkyl, lower alkyl monosubstituted to trisubstituted by lower alkoxy, carboxyl, di-lower alkylamino, phenyl or anisyl, or is etherified by lower alkyl or lower alkyl monosubstituted to trisubstituted by lower alkoxy, di-lower alkylamino, phenyl or anisyl, or 3,7-diazabicyclo[3,3.1]non-3-yl substituted in the 7-position by lower alkyl, or a pharmaceutically acceptable salt of said compound.

3. A 6-amino-penam compound of the formula I according to claim 1, in which R$_1$ is 8-azabicyclo[3.2.1]oct-8-yl, 3-azabicyclo[3.2.2]non-3-yl, 9-azabicyclo[3.3.1]non-9-yl, 7-methyl-3,7-diazabicyclo[3.3.1]non-3-yl, 2-azatricyclo[3.3.1.1$^{3,7}$]dec-2-yl, 4-azatricyclo[5.2.2.0$^{2,6}$]undec-4-yl, 4-endo-azatricyclo[5.2.2.0$^{2,6}$]undec-8-en-4-yl, 10 oxa-3-azatricyclo[5.2.1.0$^{1,5}$]dec-3-yl, 10-methyl-3,10-diaza-tricyclo[5.2.1.0$^{1,5}$]dec-3-yl or 3-endohydroxy-8-azabicyclo[3.2.1.]oct-8-yl, the hydroxyl of which is free or esterified by lower alkanoyl, carboxyl-lower alkanoyl, di-lower alkylamino-lower alkanoyl, lower alkoxycarbonyl, lower alkoxycarbonyl monosubstituted to trisubstituted by chlorine, or benzoyl, nicotinoyl, carbamoyl or toluene-sulphonyl, or is etherified by lower alkyl or lower alkyl monosubstituted to trisubstituted by lower alkoxy, di-lower alkylamino, phenyl or anisyl, and R$_2$ is carboxyl, pivaloyloxymethoxycarbonyl, lower alkoxymethoxycarbonyl, or phthalidyloxycarbonyl, or a pharmaceutically acceptable salt of said compound.

4. 6beta-[3-endo-Hydroxy-8-azabicyclo[3.2.1]oct-8-yl-methyleneamino]-penicillanic acid, the 3-hydroxyl group of which is etherfied by benzyl, benzhydryl or dimethylaminoethyl, or esterified by dimethylaminoacetyl, malonyl or trichloroethoxy-carbonyl, or a pharmaceutically acceptable salt thereof, according to claim 1.

5. A physiologically splittable ester of 6beta-[(4-endoazatricyclo[5.2.2.0$^{2,6}$]undec-8-en-4-yl)-methyleneamino]-penicillanic acid or 6beta-[4-azatricyclo[5.2.2.2.0$^{2,6}$]undec-4-yl)-methyleneamino]-penicillanic acid, or a pharmaceutically acceptable salt thereof, according to claim 1.

6. A 6-amino-penam compound of the formula I according to claim 1, in which $R_2$ is an esterified carboxyl group, which is detachable under physiological conditions, of the formula

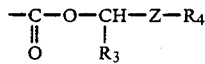

in which $R_3$ is hydrogen or lower alkyl having 1–3 carbon atoms, Z is oxygen or sulfur, $R_4$ is lower alkanoyl, lower alkanoyl substituted by hydroxyl, lower alkoxy, halogen, lower alkylthio, amino, di-lower alkylamino, carbamoyl, N,N-dimethylcarbamoyl, lower alkoxycarbonyl or lower alkylthiocarbonyl, or is lower alkyl, lower alkyl substituted by hydroxyl, lower alkoxy, halogen, lower alkylthio, amino, di-lower alkylamino, carbamoyl, N,N-di-methylcarbamoyl, lower alkoxycarbonyl or lower alkylthiocarbonyl.

7. 6β-[(3-endo-Hydroxy-8-azabicyclo[3.2.1]oct-8-yl)-methyleneamino]-penicillanic acid or a physiologically acceptable salt thereof, according to claim 1.

8. 6β-[(3-Azabicyclo[3.2.2]non-3-yl)-methyleneamino]penicillanic acid or a physiologically acceptable salt thereof, according to claim 1.

9. 6β-[(7-Methyl-3,7-diazabicyclo[3.3.1]non-3-yl)-methyleneamino]-penicillanic acid or a physiologically acceptable salt thereof, according to claim 1.

10. 6β-[(2-Azatricyclo[3.3.1.1$^{3,7}$]dec-2-yl)-methyleneamino]-penicillanic acid or a physiologically acceptable salt thereof, according to claim 1.

11. 6β-[(3-Aza-10-oxatricyclo[5.2.1.0$^{1,5}$]dec-3-yl)-methyleneamino]-penicillanic acid or a physiologically acceptable salt thereof, according to claim 1.

12. 6β-[(4-Azatricyclo[5.2.2.0$^{2,6}$]undec-4-yl)-methyleneamino]-penicillanic acid or a physiologically acceptable salt thereof, according to claim 1.

13. 6β-[(4-endo-Azatricyclo[5.2.2.0$^{2,6}$]undec-8-en-4-yl)-methyleneamino]-penicillanic acid or a physiologically acceptable salt thereof, according to claim 1.

14. Pivaloyloxymethyl 6β-[(4-endo-azatricyclo[5.2.2.0$^{2,6}$]undec-8-enyl)-methyleneamino]-penicillanate or a physiologically acceptable salt thereof, according to claim 1.

15. An antimicrobial pharmaceutical preparation comprising an effective amount of a compound according to claim 1 and pharmaceutically acceptable carriers.

16. A pharmaceutical preparation according to claim 15 wherein the antimicrobial compound alleviates the symptoms caused by infections of the respiratory tract.

17. A pharmaceutical preparation according to claim 15 in a form suitable for oral, nasal, or buccal administration.

18. A method for treating viral infections which comprises administering to a host in need of such administration an effective amount of a compound according to claim 1.

* * * * *